United States Patent [19]

Sugihara et al.

[11] Patent Number: 4,751,316
[45] Date of Patent: Jun. 14, 1988

[54] 1,5-BENZOXATHIEPIN DERIVATIVES

[75] Inventors: Hirosada Sugihara, Osaka; Minoru Hirata, Ikeda, both of Japan

[73] Assignee: Takeda Chemical Industries, Ltd., Osaka, Japan

[21] Appl. No.: 38,787

[22] Filed: Apr. 15, 1987

Related U.S. Application Data

[63] Continuation of Ser. No. 806,809, Dec. 10, 1985, Pat. No. 4,672,064, which is a continuation of Ser. No. 678,464, Dec. 5, 1984, abandoned.

[30] Foreign Application Priority Data

Dec. 14, 1983 [WO] PCT Int'l Appl. ...... PCT/JP83/436
Apr. 4, 1984 [WO] PCT Int'l Appl. ...... PCT/JP84/168
Nov. 1, 1984 [WO] PCT Int'l Appl. ...... PCT/JP84/526

[51] Int. Cl.$^4$ .......................................... C07D 327/02
[52] U.S. Cl. .................... 549/10; 540/544; 540/545; 540/553; 540/554; 540/575; 540/596; 544/145; 544/372; 546/197; 548/454
[58] Field of Search .......................................... 549/10

[56] References Cited

U.S. PATENT DOCUMENTS

| | | | |
|---|---|---|---|
| 3,306,913 | 2/1967 | Monro et al. | 549/350 |
| 3,517,031 | 6/1970 | Beereboom et al. | 549/350 |
| 3,584,002 | 6/1971 | Williams et al. | 549/350 |
| 3,647,479 | 3/1972 | Beereboom et al. | 549/350 |
| 4,188,390 | 2/1980 | Campbell | 549/350 |

OTHER PUBLICATIONS

Cerioni, "Chemical Abstracts", vol. 98, 1983, col. 98:215576.
Sugihara, et al., "Chemical Abstracts", vol. 103, col. 103:196131f.
Sugihara, et al., "Chemical Abstracts", vol. 104, col. 104:68892p.

Primary Examiner—Glennon H. Hollrah
Assistant Examiner—James H. Turnipseed
Attorney, Agent, or Firm—Wegner & Bretschneider

[57] ABSTRACT

Novel 1,5-benzoxathiepin derivatives of the formula:

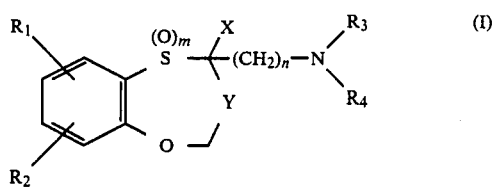

[wherein $R_1$ and $R_2$ are independently hydrogen, halogen, hydroxy, lower alkyl or lower alkoxy; $R_3$ and $R_4$ are independently hydrogen, optionally substituted lower alkyl or optionally substituted cycloalkyl or optionally substituted aralkyl, or both jointly form an optionally substituted ring together with the adjacent nitrogen atom; X is hydrogen, optionally substituted lower alkyl, optionally substituted aryl or a carboxyl group which may be esterified or amidated; Y is $>C=O$ or $>CH-OR_5$ (wherein $R_5$ is hydrogen, acyl or optionally substituted carbamoyl); m is an integer of 0 to 2; n is an integer of 1 to 6] and salts thereof exhibit serotonin $S_2$ receptor blocking activity, calcium antagonism, actions to relieve cerebral vasospasm and to improve renal circulation and diuretic and antithrombotic activities, and are of value as a prophylactic and therapeutic agent for ischemic cardiopathies, thrombosis, hypertension and cerebral circulatory disorders.

20 Claims, No Drawings

1,5-BENZOXATHIEPIN DERIVATIVES

This application is a continuation of Ser. No. 806,809, filed Dec. 10, 1985, now U.S. Pat. No. 4,672,064 which is a continuation of Ser. No. 678,464, filed Dec. 5, 1984 (abandoned July 22, 1986.

The present invention relates to novel 1,5-benzoxathiepin derivatives which are of value as pharmaceuticals, and to a process for producing the same.

The present inventors, after intensive research to create a compound having specific serotonin $S_2$ receptor blocking activity, succeeded in producing novel 1,5-benzoxathiepin derivatives which exhibit not only excellent serotonin $S_2$ receptor blocking activity but also calcium antagonism, actions to relieve cerebral vasospasm and to improve renal circulation and diuretic and antithrombotic activities and are useful as a prophylactic and therapeutic agent for ischemic cardiopathies, such as angina pectoris and myocardial infarction, thrombosis, hypertension and cerebral circulatory disorders, such as cerebral vasospasm and transient ischemic attack, and have completed the present invention.

The present invention provides novel compounds of the formula:

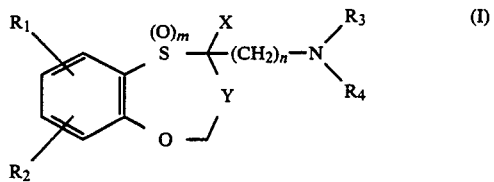

[wherein $R_1$ and $R_2$ are independently hydrogen, halogen, hydroxy, lower alkyl or lower alkoxy; $R_3$ and $R_4$ are independently hydrogen optionally substituted lower alkyl or optionally substituted cycloalkyl or optionally substituted aralkyl, or both jointly form an optionally substituted ring together with the adjacent nitrogen atom; X is hydrogen, optionally substituted lower alkyl, optionally substituted aryl or a carboxyl group which may be esterified or amidated; Y is $>C=O$ or $>CH-OR_4$ (wherein $R_5$ is hydrogen, acyl, or optionally substituted carbamoyl); m is an integer of 0 to 2; n is an integer of 1 to 6], salts thereof and a process for producing the same.

Referring to the above formula (I), the halogen represented by $R_1$ or $R_2$ includes, for example, fluorine, chlorine, bromine and iodine.

The lower alkyl group represented by $R_1$ or $R_2$ includes alkyl groups containing about 1 to 4 carbon atoms, such as methyl, ethyl, propyl, isopropyl, butyl, sec-butyl and tert-butyl, and the lower alkoxy group represented by $R_1$ or $R_2$ includes alkoxy groups containing about 1 to 4 carbon atoms, such as methoxy, ethoxy, propoxy, isopropoxy, butoxy, isobutoxy, sec-butoxy and tert-butoxy.

The case that one of $R_1$ and $R_2$ is hydrogen and the other is lower alkoxy is preferred and the case that said lower alkoxy group is attached at the 7th position of the benzoxathiepin moiety is more preferred.

The lower alkyl group represented by $R_3$ or $R_4$ includes alkyl groups containing about 1 to 4 carbon atoms, such as methyl, ethyl, propyl, isopropyl, butyl, isobutyl, sec-butyl, and tert-butyl.

The said alkyl group may be substituted by, for example, $C_{3-8}$ cycloalkyl (e.g., cyclopropyl, cyclobutyl, cyclopentyl, cyclohexyl, cycloheptyl, cyclooctyl), halogen (e.g., fluorine, chlorine, bromine), hydroxy, lower($C_{1-4}$)alkoxy (e.g., methoxy, ethoxy, propoxy, butoxy), lower($C_{1-5}$)alkanoyloxy (e.g., acetoxy, propionyloxy, butyryloxy, pivaloyloxy), mono- or di-lower($C_{1-4}$)alkylamino (e.g., methylamino, dimethylamino, methylethylamino), $C_{3-8}$ cycloalkylamino (e.g., cyclopentylamino, cyclohexylamino), lower($C_{1-5}$)alkanoylamino (e.g., acetamide, propionamide), benzamide, lower($C_{1-4}$)alkylthio (e.g., methylthio, ethylthio, propylthio, butylthio), carbamoyl, N-lower($C_{1-4}$)alkylcarbamoyl (e.g., methylcarbamoyl, ethylcarbamoyl) or N,N-di-lower($C_{1-4}$)alkylcarbamoyl (e.g., dimethylcarbamoyl, diethylcarbamoyl, methylethylcarbamoyl).

The cycloalkyl group represented by $R_3$ or $R_4$ includes cycloalkyl groups containing about 3 to 8 carbon atoms, such as cyclopropyl, cyclobutyl, cyclopentyl, cyclohexyl, cycloheptyl and cyclooctyl, and the said cycloalkyl groups may be substituted for example by lower($C_{1-4}$)alkyl (e.g., methyl, ethyl, propyl, butyl, etc.), lower($C_{1-4}$)alkoxy (e.g., methoxy, ethoxy, propoxy, isopropoxy, butoxy, etc.), lower($C_{1-5}$)alkanoylamino (e.g., acetamide, etc.) and hydroxy groups.

The aralkyl group represented by $R_3$ or $R_4$ includes phenyl-lower($C_{1-4}$)alkyl groups, such as benzyl, phenethyl, 3-phenylpropyl, α-methylbenzyl, α-ethylbenzyl, α-methylphenethyl, β-methylphenethyl and β-ethylphenethyl, whereby the phenyl group in the said phenyl-lower-alkyl groups may be substituted by 1 to 3 substituents, such as halogen (e.g., fluorine, chlorine, bromine, iodine, etc.), lower($C_{1-4}$)alkyl groups (e.g., methyl, ethyl, propyl, butyl, etc.), lower($C_{1-4}$)alkoxy groups (e.g., methoxy, ethoxy, propoxy, isopropoxy, butoxy, etc.), and methylenedioxy, amino, nitro and hydroxy groups. Examples of such substituted-phenyl-lower alkyl groups include 2-(4-chlorophenyl)ethyl, 2-(4-hydroxyphenyl)ethyl, 2-(4-methoxyphenyl)ethyl, 2-(3,4-dimethoxyphenyl)ethyl, 2-(3,4,5-trimethoxyphenyl)ethyl, 2-(3,4-methylenedioxyphenyl)ethyl, 2-(p-tolyl)ethyl, 3,4-dimethoxybenzyl, 3,4-methylenedioxybenzyl, 3,4,5-trimethoxybenzyl, 4-ethylbenzyl, 4-chlorobenzyl, etc.

The ring which $R_3$ and $R_4$ forms with the adjacent nitrogen atom includes cyclic amino groups which may contain, in addition to the said nitrogen atom, hetero atoms, such as nitrogen, oxygen and sulfur, and the cyclic amino groups include 5- to 7-membered cyclic amino groups such as pyrrolidinyl, morpholinyl, piperidyl, piperadinyl and homopiperadinyl. The said cyclic amino groups may have substituents at any substitutive positions, and such substituents include, for example, lower($C_{1-4}$)alkyl, (e.g., methyl, ethyl, propyl, butyl, etc.), aryl, aralkyl, acyl and hetero rings.

The aryl group as the substituent includes, for example, phenyl group, whereby the said phenyl group may be substituted by 1 to 3 substituents, such as halogen (e.g., fluorine, chlorine, bromine, iodine, etc.), lower($C_{1-4}$)alkyl groups (e.g., methyl, ethyl, propyl, butyl, etc.), lower($C_{1-4}$)alkoxy groups (e.g., methoxy, ethoxy, propoxy, isopropoxy, butoxy, etc.), and methylenedioxy, amino, nitro and hydroxy groups. The aralkyl as the substituent includes, for example, phenyl-lower($C_{1-4}$)alkyl such as benzyl and phenethyl, diphenyl-lower($C_{1-4}$)alkyl such as benzhydryl and triphenyl-lower($C_{1-4}$)alkyl. The acyl as the substituent includes, for example, lower($C_{1-4}$)-fatty acid residues such as lower($C_{1-4}$)alkanoyl (e.g., acetyl, propionyl and butyryl) and aromatic organic acid residues such as benzoyl and phenyl-lower($C_{1-4}$)alkanoyl and phenyl-lower($C_{1-4}$)alkenoyl (e.g., cinnamoyl). The phenyl group in the said aralkyl groups and aromatic organic acid residues may be substituted by 1 to 3 substituents, such as halogen (e.g., fluorine, chlorine, bromine, iodine, etc.), lower($C_{1-4}$)alkyl groups (e.g., methyl, ethyl, propyl, butyl, etc.), lower($C_{1-4}$)alkoxy groups (e.g., methoxy, ethoxy, propoxy, isopropoxy, butoxy, etc.), and methylenedioxy, amino, nitro and hydroxy groups. The hetero ring as the substituent includes 5- to 7-membered rings containing 1 to 3 nitrogen atoms, such as pyrrolyl, pyrazolyl, imidazolyl, pyridyl, pyrimidyl, pyridazinyl, triazinyl and azepinyl.

As regards $R_3$ and $R_4$, is preferred the case that $R_3$ and R. together with the adjacent nitrogen atom form a ring substituted by aryl, and the case that $R_3$ and $R_4$ together with the adjacent nitrogen atom form piperazinyl substituted by aryl is more preferred.

The lower alkyl group represented by X includes alkyl groups containing about 1 to 4 carbon atoms, such as methyl, ethyl, propyl, isopropyl, butyl, isobutyl, sec-butyl and tert-butyl, whereby these groups may be substituted for example by oxo, hydroxy, acyloxy and aryl. The lower alkyl group substituted by oxo includes, for example, lower($C_{1-4}$)alkanoyl, such as acetyl, propionyl and butyryl. The lower alkyl group substituted by hydroxy includes, for example, hydroxymethyl. The acyl group as the acyloxy group includes acyl groups derived from lower fatty acids, such as lower($C_{1-5}$)alkanoyl (e.g., acetyl, propionyl and butyryl), and the lower alkyl group substituted by the said acyloxy group includes, for example, acetyloxymethyl, propionyloxymethyl and butyryloxymethyl. The lower alkyl group substituted by aryl includes, for example, lower($C_{1-4}$)alkyl substituted by phenyl group such as benzyl, whereby the said phenyl group may be substituted by 1 to 3 substituents, such as halogen (e.g., fluorine, chlorine, bromine, iodine, etc.), lower($C_{1-4}$)alkyl groups (e.g., methyl, ethyl, propyl, butyl, etc.), lower($C_{1-4}$)alkoxy groups (e.g., methoxy, ethoxy, propoxy, isopropoxy, butoxy, etc.), methylenedioxy, amino, nitro and hydroxy groups.

The aryl group represented by X includes, for example, phenyl groups, whereby the said phenyl group may be substituted by 1 to 3 substituents, such as halogen (e.g., fluorine, chlorine, bromine, iodine, etc.), lower($C_{1-4}$)alkyl groups (e.g., methyl, ethyl, propyl, butyl, etc.), lower($C_{1-4}$)alkoxy groups (e.g., methoxy, ethoxy, propoxy, isopropoxy, butoxy, etc.), and methylenedioxy, amino, nitro and hydroxy groups.

The esterified carboxyl group represented by X includes, for example, lower($C_{1-4}$)alkoxycarbonyl, such as methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl, and phenyl-lower($C_{1-4}$)alkoxycarbonyl, such as benzyloxycarbonyl.

The amidated carboxyl group represented by X includes, for example, carbamoyl groups, whereby the amino group in the said carbamoyl group may be substituted by 1 to 2 substituents, such as lower($C_{1-4}$)alkyl, phenyl and phenyl-lower($C_{1-4}$)alkyl. As regards X, an esterified carboxyl group is preferred, and a lower alkoxycarbonyl group is more preferred.

The acyl group represented by $R_5$ includes, for example, lower alkanoyl groups containing about 1 to 6 carbon atoms, such as acetyl, propionyl, butyryl, valeryl and pivaloyl, and acyl groups derived from aromatic carboxylic acid, such as phenyl-lower($C_{1-6}$)alkanoyl (e.g., benzoyl, phenylacetyl and phenylpropionyl); when the aromatic ring in the said aromatic carboxylic acid is a phenyl group, said phenyl group may be substituted by 1 to 3 substituents, such as halogen (e.g., fluorine, chlorine, bromine, iodine, etc.), lower($C_{1-4}$)alkyl groups (e.g., methyl, ethyl, propyl, butyl, etc.), lower($C_{1-4}$)alkoxy groups (e.g., methoxy, ethoxy, propoxy, isopropoxy, butoxy, etc.), and methylenedioxy, amino, nitro and hydroxy group.

The optionally substituted carbamoyl group represented by $R_5$ includes, for example, carbamoyl, whereby the amino group in the said carbamoyl group may be substituted by lower alkyl (e.g., methyl, ethyl, propyl, butyl, etc.), phenyl, phenyl-lower($C_{1-4}$)alkyl (e.g., benzyl, phenethyl, etc.), etc. The phenyl group in the said phenyl and phenyl-lower-alkyl groups may be substituted by 1 to 3 substituents, such as halogen (e.g., fluorine, chlorine, bromine, iodine, etc.), lower($C_{1-4}$)alkyl groups (e.g., methyl, ethyl, propyl, butyl, etc.), lower($C_{1-4}$)alkoxy groups (e.g., methoxy, ethoxy, propoxy, isopropoxy, butoxy, etc.), and methylenedioxy, amino, nitro and hydroxy groups. As regards Y, is preferred a hydroxymethylene group.

The sulfur atom in the formula (I) forms, for example, sulfide, sulfoxide and sulfone, depending upon the value of m. The case that m is 0 is preferred.

The group —$(CH_2)_n$— in the formula (I) forms, for example, methylene, ethylene, trimethylene, tetramethylene, pentamethylene and hexamethylene, depending upon the value of n. Among these groups, trimethylene is preferred.

Salts of the compounds (I) include pharmaceutically acceptable salts, such as salts with inorganic acids being exemplified by hydrochloride, hydrobromide, sulfate, nitrate, phosphate, etc., and salts with organic acids being exemplified by acetate, tartarate, citrate, fumarate, maleate, toluenesulfonate, methanesulfonate, etc.

Preferred compounds (I) are those of the formula:

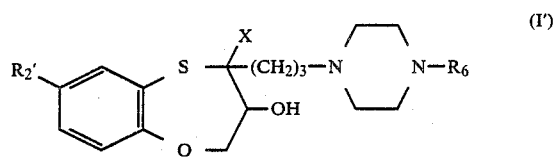

(I')

wherein $R_6$ is phenyl which may be substituted by 1 to 3 members of halogen, $C_{1-4}$ alkyl, $C_{1-4}$ alkoxy, methylenedioxy, amino, nitro or hydroxy, $R_{2'}$ is $C_{1-4}$ alkoxy and X is $C_{1-4}$ alkoxycarbonyl, and their pharmaceutically acceptable salts.

Other preferred compounds (I) are those of the formula:

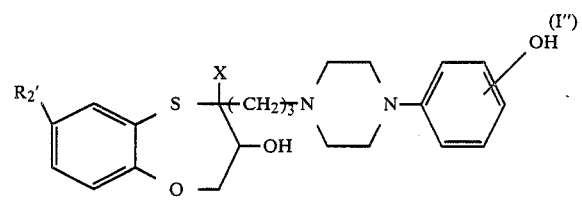

(I'')

wherein $R_{2'}$ is hydroxy or lower ($C_{1-4}$) alkoxy, and X is lower ($C_{1-4}$) alkoxycarbonyl, and their pharmaceutically acceptable salts.

Hydroxy group as the substituent of hydroxyphenylpiperazinyl group may be attached to any position (i.e. ortho, meta, para) of phenyl group, but preferred is paraposition of phenyl group.

Among the compunds (I''), the compounds of the formula (I'') wherein the group

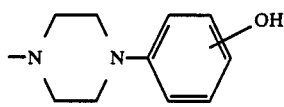

is 4-(4-hydroxyphenyl)piperazin-1-yl and $R_{2'}$ is lower ($C_{1-4}$) alkoxy are most preferable. Such compounds as those of the formula (I'') having hydroxy group as a substituent to phenylpiperazinyl group have more excellent $S_2$ receptor blocking activity.

The compound (I) of the present invention can be produced, for example, by subjecting a compound of the formula:

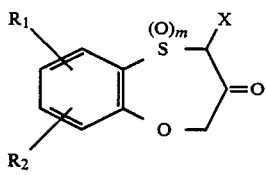

[wherein the symbols are as defined hereinbefore] and a compound (III) of the formula:

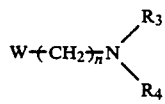

[wherein n, $R_3$ and $R_4$ are as defined hereinbfore; W is halogen or a group represented by the formula R—SO$_2$—O— (wherein R is lower($C_{1-4}$)alkyl, phenyl or p-tolyl)] to a condensation reaction, a condensation reaction and thereafter a reduction reaction, or a condensation reaction and thereafter a reduction reaction, followed by an acylation or carbamoylation reaction.

The said condensation reaction is normally carried out in the presence of a base. The base includes, for example, inorganic bases, such as potassium carbonate, potassium hydrogencarbonate, sodium carbonate, sodium methoxide, sodium hydride and lithium diisopropylamide, and organic amines, such as triethylamine, pyridine and 1,8-diazabicyclo[5,4,0]-7-undecene. On this occasion, the reaction can also be allowed to proceed advantageously, for example, by using sodium iodide, potassium iodide, etc. as a catalyst. The above reaction can be normally conducted in an organic solvent (e.g., acetone, 2-butanone, acetonitrile, N,N-dimethylformamide, methylene chloride, benzene, toluene, tetrahydrofuran, dioxane, etc.) at a reaction temperature in the range of −20° C. to +150° C., preferably +20° C. to +120° C.

As a means of reducing the compound (I) wherein Y is >C=O as obtained by the condensation reaction, there may be mentioned reaction conditions of reduction with a metal hydride compound, such as lithium aluminum hydride, lithium borohydride, lithium cyanoborohydride, sodium borohydride, sodium cyanoborohydride and tri-tert-butoxylithium aluminum hydride; reduction with metallic sodium, metallic magnesium, etc. and alcohols; catalytic reduction using a metal, such as platinum, palladium and rhodium, or a mixture thereof with an arbitrary support as a catalyst; reduction with a metal, such as iron and zinc, and an acid, such as hydrochloric acid and acetic acid; electrolytic reduction; reduction with a reducing enzyme; reduction with a boron hydride compound, such as diborane, or a complex compound of a boron hydride compound and an amine, such as boranetrimethylamine; and so forth. The above reaction is normally carried out in the presence of water or an organic solvent (e.g., methanol, ethanol, ethyl ether, dioxane, methylene chloride, chloroform, benzene, toluene, acetic acid, dimethylformamide, dimethylacetamide, etc.), and the reaction temperature varies with the reduction means employed, but generally is preferably in the range of −20° C. to +100° C.

The acylation or carbamoylation reaction subsequent to condensation and reduction can be carried out by use of ordinary means of an acylation or carbamoylation reaction of alcohol derivatives. The means of such acylation reaction can be realized, for example, by reacting with a reactive derivative (e.g., acid anhydride, acid halide, etc.) of an organic acid corresponding to $R_5$ in the presence of an organic amine, such as pyridine, triethylamine and N,N-dimethylaniline, or an inorganic base, such as sodium carbonate, potassium carbonate and sodium hydrogencarbonate. The above reaction is normally carried out in an organic solvent (e.g., methanol, ethanol, ethyl ether, dioxane, methylene chloride, toluene, dimethylformamide, pyridine, etc.), and the reaction temperature generally is preferably in the range of −20° C. to +100° C. The carbamoylation can be realized, for example, by reacting an alcohol derivative as obtained in the reduction reaction with an isocyanate derivative (e.g., methyl isocyanate, ethyl isocyanate, phenyl isocyanate, p-chlorophenyl isocyanate, etc.) corresponding to $R_5$. The above reaction is normally carried out in an appropriate solvent (e.g., methanol, ethanol, acetonitrile, dioxane, tetrahydrofuran, methylene chloride, chloroform, toluene, N,N-dimethylformamide, etc.), and the reaction temperature generally is preferably in the range of −20° C. to +150° C.

Also, the compound (I) of the present invention can be obtained, for example, by reacting a compound of the formula:

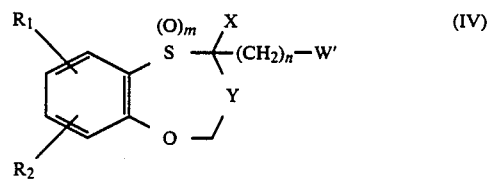

[wherein W' is halogen or a group represented by the formula R'—SO$_2$—O— (wherein R' is lower($C_{1-4}$)alkyl, phenyl or p-tolyl); other symbols are as defined hereinabove] with an amine derivative of the formula:

(V)

[wherein $R_3$ and $R_4$ are as defined hereinabove]. The reaction of the compound (IV) with the amine derivative (V) can be carried out in an appropriate solvent (e.g., methanol, ethanol, dioxane, acetonitrile, tetrahydrofuran, N,N-dimethylformamide, N,N-dimethylacetamide, methylene chloride, dimethylsulfoxide and an arbitrary solvent mixture thereof). The reaction temperature is preferably in the range of 0° C. to +150° C., and for the purpose of increasing the reaction rate, organic base, such as triethylamine, pyridine and N,N-dimethylaniline, or an inorganic base, such as potassium carbonate, sodium carbonate and sodium hydrogencarbonate may be added as a catalyst.

After the said reaction, a compound of the formula (I) wherein Y is $>C=O$ can be subjected to an acylation or carbamoylation reaction subsequent to the above-mentioned reduction method or reduction reaction to derive into a compound of the formula (I) wherein Y is $>CH-OR_5$.

The compound (I) of the present invention can also be produced, for example, by allowing a compound of the formula:

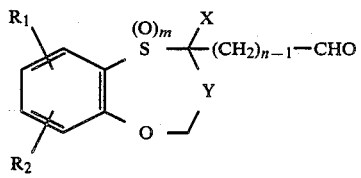

(VI)

[wherein each of the symbols is as defined hereinbefore] to undergo condensation with the compound (V) under reductive conditions.

The said reductive conditions include reaction conditions of catalytic reduction using a metal, such as platinum, palladium, Raney nickel and rhodium, or a mixture thereof with an arbitrary support as a catalyst; reduction with a metal hydride compound, such as lithium aluminum sodium borohydride and sodium cyanoborohydride; reduction with metallic sodium, metallic magnesium, etc. and alcohols; reduction with a metal, such as iron and zinc, and an acid, such as hydrochloric acid and acetic acid; electrolytic reduction; reduction with a reducing enzyme, and so forth. The above reaction is normally carried out in the presence of water or an organic solvent (e.g., methanol, ethanol, ethyl ether, dioxane, methylene chloride, chloroform, benzene, toluene, acetic acid, dimethylformamide, dimethylsulfoxide, etc.), and the reaction temperature varies with the means of reduction employed, and generally is preferably in the range of −20° C. to +100° C. This reaction can be conducted at atmospheric pressure to achieve the desired object satisfactorily but may also be carried out under pressure or under reduced pressure according to the circumstances.

Furthermore, the compound (I) of the present invention can be produced, for example, by subjecting a compound of the formula:

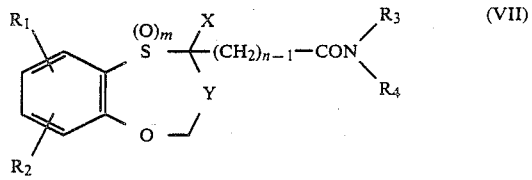

(VII)

[wherein each of the symbols is as defined hereinabove] to a reaction of reducing the amide group. The said reduction reaction can be carried out by use of means of reduction, such as reduction with lithium aluminum hydride, sodium dihydro-bis[2-methoxyethoxy]aluminate, sodium acetoxyborohydride, aluminum hydride, diborane and alkyl borane. The above reaction is normally carried out in the presence of an organic solvent (e.g., ethyl ether, tetrahydrofuran, dioxane, toluene, benzene, etc.), and the reaction temperature varies with means of reduction employed, and generally is preferably in the range of −20° C. to +120° C. In the case of a compound of the formula (VII) wherein X is, for example, esterified or amidated carboxyl and Y is $>C=O$, in the said reduction reaction, these functional groups can be reduced simultaneously, and the desired amide group alone can also be reduced by protecting the carbonyl group or by selecting a reducing agent, as the case may be.

A sulfoxide or sulfone compound of the formula (I) wherein m is 1 or 2 can also be produced by oxidizing the corresponding sulfide compound. The said oxidation reaction is carried out, for example, by acting an organic peracid (e.g., m-chloroperbenzoic acid, peracetic acid, etc.) or inorganic acid (e.g., hydrogen peroxide, periodic acid, etc.). The above reaction is normally carried out in the presence of an organic solvent (e.g., methanol, ethanol, dioxane, dichloromethane, etc.) within the temperature range of −20° C. to +100° C.

The compound of the formula (I) wherein $R_1$ or $R_2$ is hydroxy can be produced by the above-mentioned reactions, and can also be produced, for example, by reacting the compound of the formula (IV) wherein $R_1$ or $R_2$ is a protected hydroxy group (e.g. benzyloxy, methoxymethyloxy) with the compound (V) in the same manner as described in the above-mentioned reaction of the compounds (IV) and (V), and then subjecting the obtained compound of the formula (I) wherein $R_1$ or $R_2$ is the protected hydroxy group to a deprotection reaction.

The deprotection reaction includes catalytic reduction using a metal, such as platinum, palladium or rhodium, or a mixture thereof with an arbitrary support as a catalyst (when the protected hydroxy group is benzyloxy), and hydrolysis using an inorganic acid, such as hydrochloric acid, sulfuric acid or phosphoric acid or an organic acid, such as formic acid or acetic acid as a catalyst (when the protected hydroxy group is methoxymethyloxy).

The above catalytic reduction reaction is normally carried out in the presence of water or an organic solvent (e.g., methanol, ethanol, ethyl ether, dioxane), and the reaction temperature varies with means of reduction employed but generally is preferably in the range of −20° C. to +100° C. This reaction can be conducted at atmospheric pressure to achieve the desired object satisfactorily, but may also be carried out under pressure or under reduced pressure according to the circumstances.

The above hydrolysis reaction is normally carried out in the presence of water or an organic solvent (e.g., methanol, ethanol, dioxane, dichloromethane) and ordinarily in the temperature range of −20° C. to +100° C.

The object compound (I) of the present invention thus obtained can be isolated from the reaction mixture by utilizing conventional separation and purification means, for example, means such as extraction, concentration, neutralization, filtration, recrystallization, column chromatography and thin layer chromatography.

In the case of a compound of the formula (I) wherein Y is >CH—OR$_5$, there exist at least two stereoisomers. These individual isomers and a mixture thereof, naturally, both fall within the scope of the present invention, and such isomers can also be produced individually, if desired. For example, a single optical isomer of the compound (I) can be obtained by carrying out the above reaction using a single isomer each of the starting compounds (IV) and (VI). When the product is a mixture of not less than two kinds of isomers, it can be separated into individual isomers by a usual separation technique, for example, separation means such as a method of forming salts with optically active acids (e.g., camphorsulfonic acid, tartaric acid, dibenzoyltartaric acid, malic acid, etc.), a variety of chromatographic techniques and fractional recrystallization.

The compounds of the present invention, namely the 1,5-benzoxathiepin derivatives represented by the formula (I), exhibit specific serotonin S$_2$ receptor blocking activity, calcium antagonism, actions to relieve cerebral vasospasm and to improve renal circulation, diuretic and antithrombotic activities in animals, in particular, mammals (e.g., human, pigs, dogs, cats, rabbits, guinea pigs, rats, etc.), and are useful, for example, as drugs for prevention and treatment of ischemic cardiopathies, such as angina pectoris and myocardial infarction, thrombosis, hypertension and cerebral circulatory disorders, such as cerebral vasospasm and transient ischemic attack. The compounds of the present invention are of low toxicity, well absorbed even on oral administration and highly stable, and when they are used as the abovementioned drugs, therefore, they can be safely administered orally or parenterally, per se or in admixture with suitable, pharmaceutically acceptable carriers, excipients or diluents in various pharmaceutical formulations, such as powders, granules, tablets, capsules and injectable solutions. While the dosage level varies depending upon the conditions of the diseases to be treated as well as the administration route, in the case of administration to human adult for the purpose of treatment of ischemic cardiopathies or hypertension, for example, the compounds may be desirably administered orally at a single dose of, normally about 0.1 to 10 mg/kg, preferably about 0.3 to 3 mg/kg, or intravenously at a single dose of about 0.003 to 0.1 mg/kg, preferably about 0.01 to 0.1 mg/kg, about once to 3 times daily according to the conditions.

In the case of administration to human adult for the purpose of treatment of cerebral circulatory disorders, for example, the compounds may be desirably administered orally at a single dose of, normally about 0.1 to 50 mg/kg, preferably about 0.3 to 30 mg/kg, or intravenously at a single dose of about 0.003 to 10 mg/kg, preferably about 0.01 to 1 mg/kg, about once to 3 times per day according to the conditions.

The starting compounds (II), (IV), (VI) and (VII) can be produced, for example, by the methods as illustrated in the following reaction schema.

(i) Compound (II)

(a) In the case of X being aryl which may be substituted or carboxyl which may be esterified or amidated:

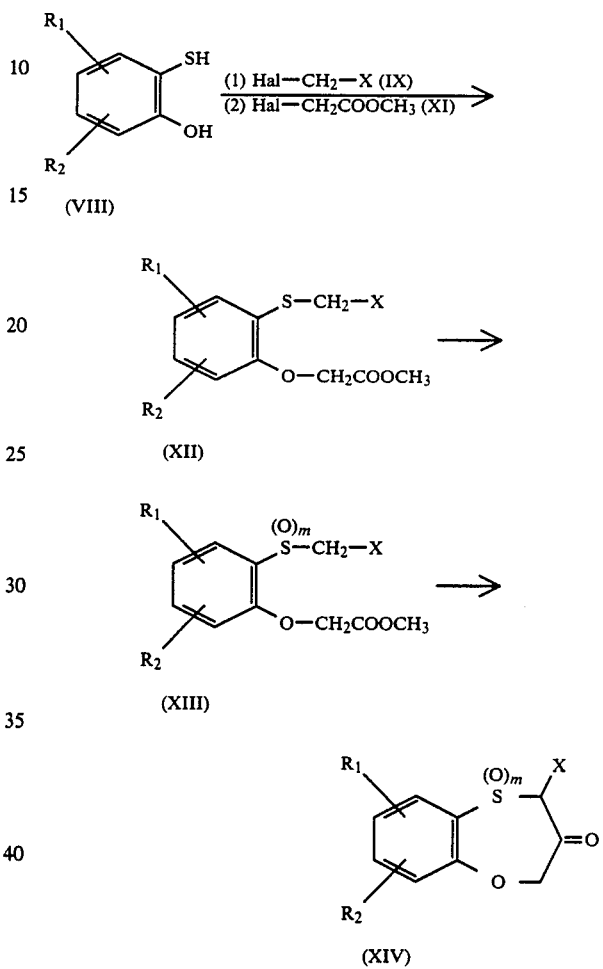

(b) In the case of X being lower alkyl which may be substituted:

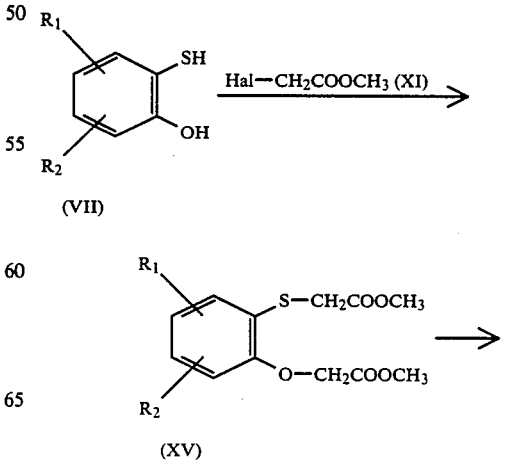

-continued
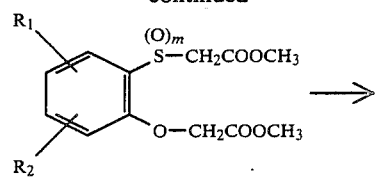
(XVI)
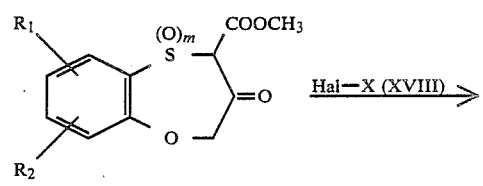 Hal—X (XVIII) →
(XVII)
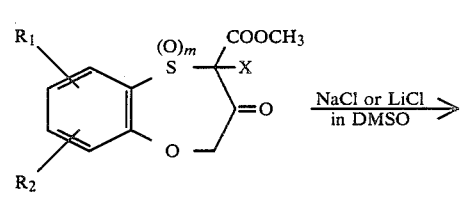 NaCl or LiCl in DMSO →
(XIX)
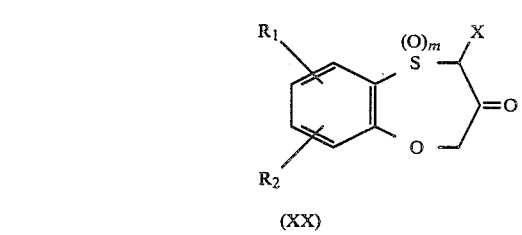
(XX)
(c) In the case of X being hydrogen:
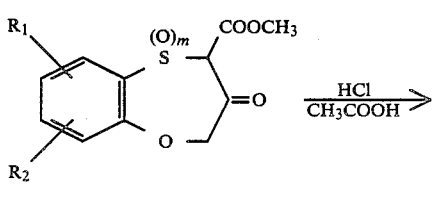 HCl/CH₃COOH →
(XVII)
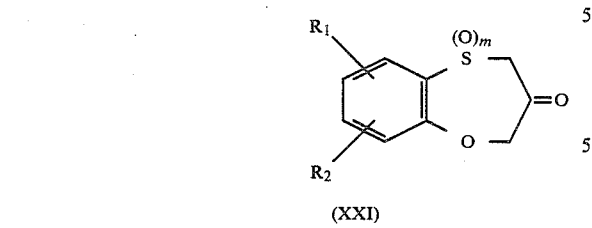
(XXI)
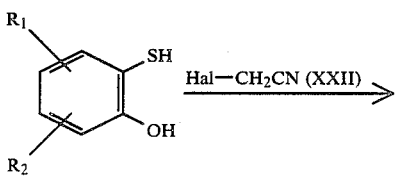 Hal—CH₂CN (XXII) →
(VIII)
-continued
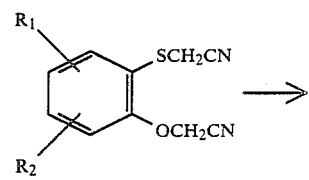
(XXIII)
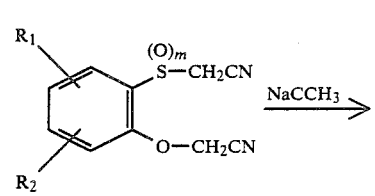 NaCCH₃ →
(XXIV)
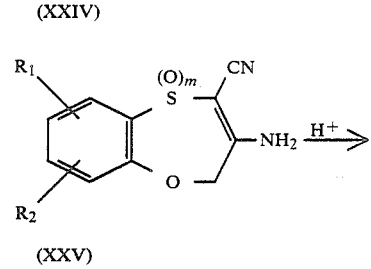 H⁺ →
(XXV)
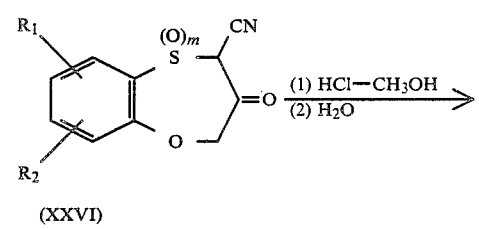 (1) HCl—CH₃OH / (2) H₂O →
(XXVI)
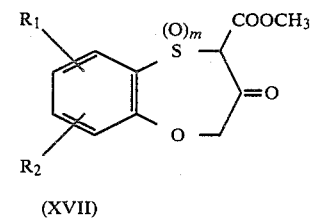
(XVII)
(ii) Compound (IV)
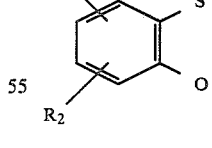 Hal—(CH₂)ₙ—W' (XXVII) →
(XIV)
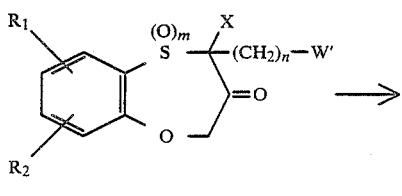 →
(XXVIII)

-continued

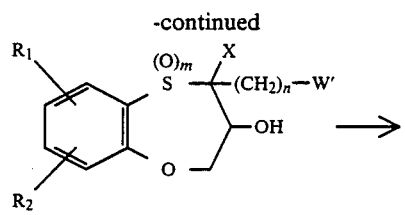

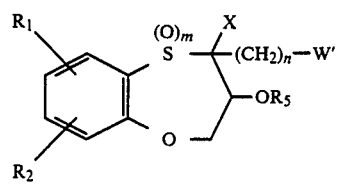

(iii) Compound (VI)

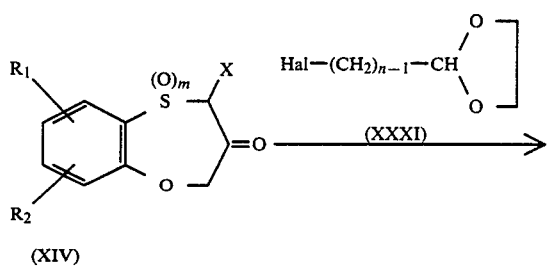

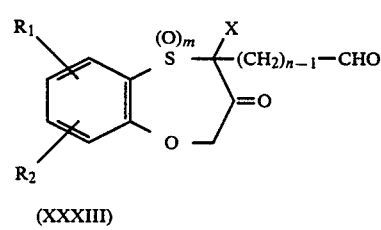

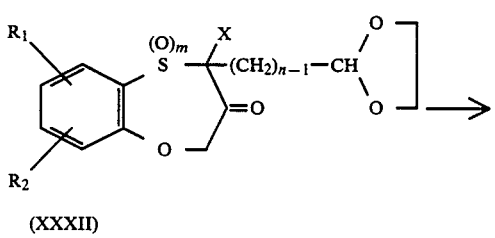

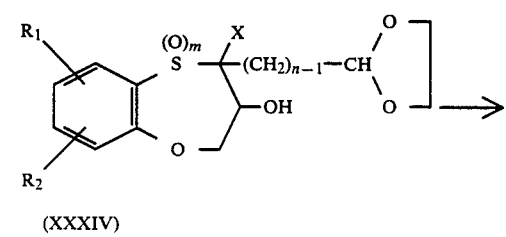
(XXXIV)

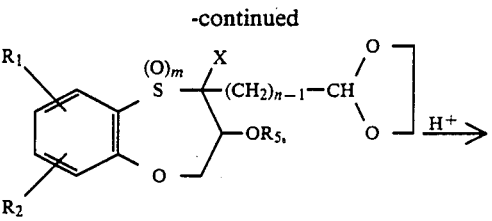
(XXXV)

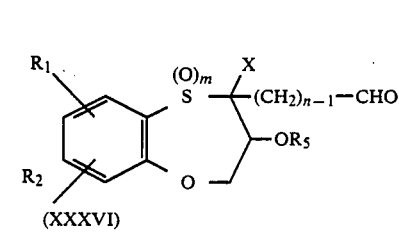
(XXXVI)

(iv) Compound (VII)

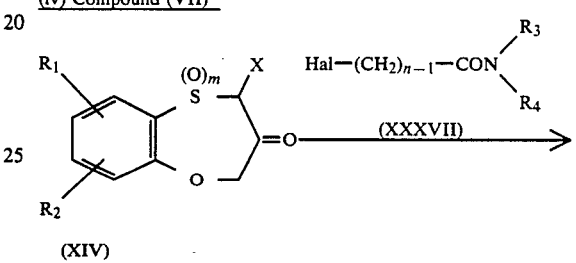

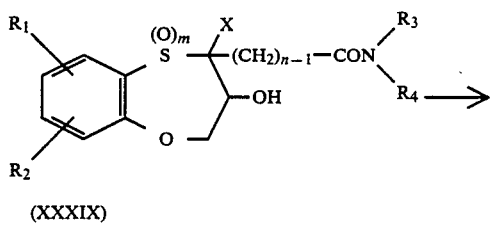
(XXXVIII)

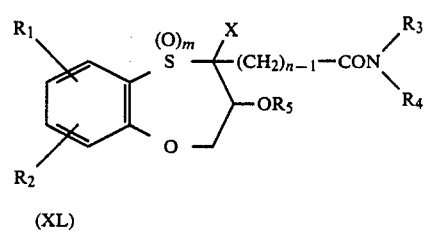
(XXXIX)

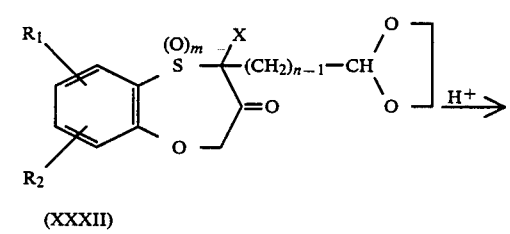
(XL)

In the above reaction schema, Hal is halogen (e.g., bromine, chlorine, etc.); and other symbols are as defined hereinbefore.

In cases in which a compound of the formula (II) wherein X is aryl which may be substituted or carboxyl which may be esterified or amidated is produced, the compound (XII) can be obtained by reacting the compound (VIII) used as a starting compound with the compound (IX) in a suitable organic solvent (e.g., acetone, acetonitrile, benzene, toluene, methylene chloride, N,N-dimethylformamide, etc.), followed by reaction with the compound (XI). The said reaction is normally carried out preferably by allowing a base such as potassium carbonate and sodium hydrogencarbonate to coexist in the system for the purpose of accelerating the reaction rate, and the reaction temperature normally is preferably in the range of 0° C. to +120° C.

A compound of the formula (XIII) wherein m is 1 or 2 can be produced by oxidizing the compound (XII). The said oxidation reaction is carried out, for example, by acting an organic peracid (e.g., m-chloroperbenzoic acid, peracetic acid, etc.) or inorganic oxidizing agent (e.g., hydrogen peroxide, periodic acid, etc.). The above reaction is normally conducted in the presence of water or an organic solvent (e.g., methanol, ethanol, dioxane, dichloromethane, etc.) and ordinarily in the temperature range of about −20° C. to +100° C. A compound of the formula (XIII) wherein m is 0 can be used in the subsequent reaction without being subjected to the said oxidation reaction.

The ring-closure reaction to yield the compound (XIV) from the compound (XIII) is normally carried out in an organic solvent (e.g., N,N-dimethylformamide, acetonitrile, methanol, dimethylsulfoxide, etc.), and is allowed to proceed advantageously in the presence of a base (e.g., sodium methoxide, sodium ethoxide, potassium tert-butoxide, sodium hydride, etc.). The reaction temperature normally is preferably in the range of −20° to +100° C. In cases in which the compound (XIV) is obtained in the form of an alkali metal salt in the above reaction, such a compound is neutralized with, for example, acetic acid, hydrochloric acid, sulfuric acid, etc., and the compound (XIV) can be isolated by conventional methods.

In the case of a compound of the formula (II) wherein X is lower alkyl which may be substituted, the compound (XX) can be obtained by reacting the compound (VIII) with the compound (XI) to give the compound (XV), then, if necessary, converting the compound (XV) into the compound (XVI), subjecting the compound (XVI) to a ring-closure reaction, followed by alkylation, and subjecting the alkylated compound to a reaction of removing the ester group.

The reaction between the compounds (VIII) and (XI) can be carried out in the same manner as the reaction of the compound (VIII) with the compound (IX). The conversion of the compound (XV) into the compound (XVI) can be conducted in the same manner as the conversion of the compound (XII) into the compound (XIII). The ring-closure reaction of (XVI)→(XVII) can be carried out in the same manner as the reaction of (XIII)→(XIV).

The reaction between the compounds (XVII) and (XVIII) can be carried out in an appropriate organic solvent (e.g., acetone, 2-butanone, acetonitrile, N,N-dimethylformamide, dimethylsulfoxide, benzene, toluene, tetrahydrofuran, etc.) in the coexistence of a base (e.g., sodium carbonate, potassium carbonate, sodium hydrogencarbonate, sodium hydride, sodium methoxide, triethylamine, pyridine, etc.). In such a case, the reaction can be allowed to proceed smoothly by adding an iodine compound, such as potassium iodide and sodium iodide, as a catalyst. The reaction normally is carried out preferably at a temperature in the range of −20° C. to +150° C.

The reaction of (XIX)→(XX) is allowed to proceed by heating the compound (XIX) in an appropriate organic solvent (e.g., dimethylsulfoxide, N,N-dimethylformamide, N,N-dimethylacetamide, etc.) in the coexistence of a salt (e.g., sodium chloride, lithium chloride, calcium chloride, sodium bromide, etc.) at a temperature in the range of +50° C. to +160° C. in accordance with an ordinary reaction of removing the ester group.

In the case of a compound of the formula (II) wherein X is hydrogen, the compound (XXI) can be obtained by subjecting the compound (XVII) to the same reaction as the reaction of (XIX)→(XX).

Also, the compound (XVII) can be produced by reacting the compound (VIII) used as a starting compound with the compound (XXII), then oxidizing the sulfur atom to give the compound (XXIV), if desired, subjecting it to the same ring-closure reaction as the above-mentioned reaction and further subjecting the resulting compound (XXV) to an ordinary hydrolysis reaction.

The reaction between the compounds (XIV) and (XXVII) can be carried out in the same manner as the reaction of the compound (XVII) with the compound (XVIII). The compound (XXIX) can be obtained by subjecting the compound (XXVIII) to a reduction reaction. In the said reduction reaction, there may be mentioned reaction conditions of reduction with a metal hydride compound, such as lithium aluminum hydride, lithium borohydride, lithium cyanoborohydride, sodium borohydride, sodium cyanoborohydride, and tri-tertbutoxylithium aluminum hydride; reduction with metallic sodium, metallic magnesium, etc. and alcohols; catalytic reduction using a metal, such as platinum, palladium and rhodium, and a mixture thereof with an arbitrary support as a catalyst; reduction with a metal, such as iron and zinc, and an acid, such as hydrochloric acid and acetic acid; electrolytic reduction; reduction with a reducing enzyme; reduction with a boron hydride compound, such as diborane, or a complex compound of a boron hydride compound and an amine, such as borane-trimethylamine, and so forth. The above reaction is normally carried out in the presence of water or an organic solvent (e.g., methanol, ethanol, ethyl ether, dioxane, methylene chloride, chloroform, benzene, toluene, acetic acid, dimethylformamide, dimethylacetamide, etc.), and the reaction temperature varies with means of reduction employed, and generally is preferably in the range of −20° C. to +100° C.

The reaction of (XXIX)→(XXX) can be carried out using ordinary means of an acylation or carbamoylation reaction of alcohol derivatives. The said means of an acylation reaction can be realized, for example, by reacting a reactive derivative (e.g., acid anhydride, acid halide, etc.) of an organic acid corresponding to $R_5$ with the compound (XXIX) in the presence of an organic base (e.g., pyridine, triethylamine, N,N-dimethylaniline, etc.).

The above reaction is normally carried out in an organic solvent (e.g., methanol, ethanol, ethyl ether, dioxane, methylene chloride, toluene, dimethylformamide, pyridine, etc.), and the reaction temperature generally is preferably in the range of −20° C. to +100° C. The carbamoylation reaction can be carried out, for example, by reacting an alcohol derivative (XXIX) as obtained in the reduction reaction with an isocyanate derivative (e.g., methyl isocyanate, ethyl isocyanate, phenyl isocyanate, p-chlorophenyl isocyanate, etc.). The above reaction is normally conducted in an appropriate organic solvent (e.g., methanol, ethanol, acetonitrile, dioxane, tetrahydrofuran, methylene chloride, chloroform, toluene, N,N-dimethylformamide, etc.), and the reaction temperature generally is preferably in the range of −20° C. to +150° C.

The reaction of (XIV) with (XXXI) can be carried out in the same manner as the reaction of (XVII) and (XVIII). The compound (XXXIII) can be obtained by hydrolyzing the compound (XXXII) with a dilute mineral acid (e.g., hydrochloric acid, sulfuric acid, etc.). The compound (XXXIV) can be obtained by subjecting the compound (XXXII) to the same reduction reaction as the reduction reaction of (XXVIII)→(XXIX), and the reaction of (XXXIV)→(XXXV) can be carried out in the same manner as the reaction of (XXIX)→(XXX). The compound (XXXVI) can be obtained by subjecting the compound (XXXV) to the same reaction as the reaction of (XXXII)→(XXXIII).

The reaction between the compounds (XIV) and (XXXVII) can be carried out in the same manner as the reaction of the compound (XVII) with the compound (XVIII). The reaction of (XXXVIII)→(XXXIX) can be conducted in the same manner as the reaction of (XXVIII)→(XXIX), while the reaction of (XXXIX)→(XL) can be carried out in the same manner as the reaction of (XXIX)→(XXX).

The compound of the formula (IV) wherein $R_1$ or $R_2$ is a protected hydroxy group can be produced according to the above-mentioned method for preparing the compound (IV).

In the above processes for producing the compound (I) and intermediates thereof, the compounds which are used in the reactions may be used in the form of salts, such as inorganic acid salts being exemplified by hydrochloride, hydrobromide, sulfate, nitrate, and phosphate, etc., organic acid salts being exemplified by acetate, tartarate, citrate, fumarate, maleate, toluenesulfonate, methanesulfonate, etc., metal salts being exemplified by sodium salt, potassium salt, calcium salt, aluminum salt, etc., and salts with bases being exemplified by triethylamine salt, guanidine salt, ammonium salt, hydrazine salt, guinine salt, cinchonine salt, etc., so long as they do not interfere with such reactions.

The following Reference Examples, Examples, Experiment Examples and Preparation Examples illustrate the present invention in more detail, but they are by no means limitative of the present invention.

REFERENCE EXAMPLE 1

In 350 ml of acetone are dissolved 44.7 g of 2-mercapto-4-methoxyphenol and 88 g of methyl bromoacetate, and 88 g of anhydrous potassium carbonate is added to the solution, followed by stirring at room temperature for 5 hours and then heating under reflux for 5 hours. After the mixture is cooled, the inorganic substance is filtered off, and the filtrate is concentrated under reduced pressure. The residue is recrystallized from ethyl acetatehexane to give 65 g of colorless crystals of methyl 4-methoxy-2-methoxycarbonylmethylthiophenoxyacetate, melting point of 78° C.

Elemental analysis, for $C_{13}H_{16}O_6S$ Calcd.: C, 51.99; H, 5.37 Found: C, 52.18; H, 5.37

REFERENCE EXAMPLE 2

In 300 ml of N,N-dimethylformamide is dissolved 94.4 g of methyl 4-methoxy-2-methoxycarbonylmethylthiophenoxyacetate, and 67 g of 28% sodium methoxide is added dropwise to the solution under ice-cooling with stirring. The reaction mixture is stirred for 1 hour and poured in ice-cold water containing dilute hydrochloric acid, and the precipitate is collected by filtration, washed with water, dried and then recrystallized from ethyl acetate-hexane to give 58.7 g of colorless crystals of methyl 7-methoxy-3-oxo-3,4-dihydro-2H-1,5-benzoxathiepin-4-carboxylate, m.p. 79°–81° C.

Elemental analysis, for $C_{12}H_{12}O_5S$: Calcd.: C, 53.72; H, 4.51 Found: C, 53.72; H, 4.40

REFERENCE EXAMPLE 3

In 300 ml of acetone are dissolved 28 g of 2-mercapto-4-methoxyphenol and 25 g of chlorodiethylacetamide, and 25 g of anhydrous potassium carbonate is added to the solution, followed by stirring at room temperature under a nitrogen gas stream for 3 hours. Then, 28 g of methyl bromoacetate and 25 g of anhydrous potassium carbonate are added to the reaction mixture, followed by heating under reflux for 5 hours. After the mixture is cooled, the inorganic substance is filtered off, and the filtrate is concentrated under reduced pressure. The residue is purified by column chromatography on silica gel (eluent: hexane:ethyl acetate=1:1) to give 45 g of a colorless oily material of methyl 2-diethylcarbamoylmethylthio-4-methoxyphenoxyacetate.

Elemental analysis, for $C_{16}H_{23}NO_5S$: Calcd.: C, 56.29; H, 6.79; N, 4.10, Found: C, 56.23; H, 6.77; N, 4.18.

REFERENCE EXAMPLE 4

In 160 ml of N,N-dimethylformamide is dissolved 43 g of methyl 2-diethylcarbamoylmethylthio-4-methoxyphenoxyacetate, and 30 g of 28% sodium methoxide is added dropwise to the solution under ice-cooling and under a nitrogen gas stream with stirring, followed by stirring for 6 hours. The reaction mixture is poured into ice-cold water containing 15 ml of acetic acid, followed by extraction with ethyl acetate. The organic layers are combined, washed with water and dried, and the solvent is evaporated off under reduced pressure. The resulting residue is purified by column chromatography on silica gel (eluent: hexane:ethyl acetate=1.1), followed by recrystallization from ethyl acetate to give colorless prisms of 7-methoxy-3-oxo-3,4-dihydro-2H-1,5-benzoxathiepin-4-diethylcarboxamide, m.p. 112°–113° C.

Elemental analysis, for $C_{15}H_{19}NO_4S$: Calcd.: C, 58.23; H, 6.19; N, 4.53, Found: C, 58.17; H, 6.06; N, 4.54.

REFERENCE EXAMPLE 5

In 600 ml of acetone are dissolved 60 g of 2-mercapto-4-methoxyphenol and 67 g of chloroacetonitrile, and 125 g of anhydrous potassium carbonate is added to the solution at room temperature under a nitrogen gas stream with stirring, followed by stirring at room temperature for 3 hours and then by heating under reflux for 5 hours. After the reaction mixture is cooled, the inorganic substance is filtered off, and the filtrate is concentrated under reduced pressure. The residue is recrystallized from ethanol to give colorless prisms of 2-cyanomethylthio-4-methoxyphenoxyacetonitrile. Yield of 65 g, m.p. of 53°–54° C.

Elemental analysis, for $C_{11}H_{10}N_2O_2S$: Calcd.: C, 56.39; H, 4.30; N, 11.96, Found: C, 56.57; H, 4.32; N, 11.78.

REFERENCE EXAMPLE 6

In 120 ml of N,N-dimethylformamide is dissolved 30 g of 2-cyanomethylthio-4-methoxyphenoxyacetonitrile, and 30 g of 28% sodium methoxide is added dropwise to the solution under ice-cooling and under a nitrogen gas stream with stirring, followed by stirring for 2 hours.

The reaction mixture is poured in ice-cold water containing 12 g of acetic acid, and the precipitate is collected by filtration, washed with water and recrystallized from chloroform to give colorless prisms of 3-amino-7-methoxy-2H-1,5-benzoxathiepin-4-carbonitrile. Yield of 19.5 g, m.p. of 203°–205° C.

REFERENCE EXAMPLE 7

In 60 ml of ethanol is suspended 6.0 g of 3-amino-7-methoxy-2H-1,5-benzoxathiepin-4-carbonitrile, and 18 ml of concentrated hydrochloric acid is added to the suspension, followed by stirring at 80° C. to 90° C. for 30 minutes. After the reaction mixture is cooled, ammonium chloride, which separates out, is filtered off, and the filtrate is concentrated under reduced pressure. The residue is recrystallized from ethyl acetate-hexane to give colorless prisms of 7-methoxy-3-oxo-3,4-dihydro-2H-1,5-benzoxathiepin-4-carbonitrile. Yield of 5.1 g, m.p. of 132°–133° C.

Elemental analysis, for $C_{11}H_9NO_3S$: Calcd.: C, 56.16; H, 3.86; N, 5.95, Found: C, 56.08; H, 3.79; N, 5.85.

REFERENCE EXAMPLE 8

In 200 ml of methanol is dissolved 15 g of 7-methoxy-3-oxo-3,4-dihydro-2H-1,5-benzoxathiepin-4-carbonitrile, and the solution is saturated with dried hydrogen chloride, followed by allowing the solution to stand at room temperature for 4 days. 10 ml of water is added to the reaction solution, the mixture is allowed to stand overnight and concentrated under reduced pressure. The residue is purified by column chromatography on silica gel (eluent; chloroform) to give 6.0 g of methyl 7-methoxy-3-oxo-3,4-dihydro-2H-1,5-benzoxathiepin-4-carboxylate as obtained in Reference Example 2, together with 6.0 g of the starting material being recovered.

REFERENCE EXAMPLE 9

A mixture of 2.0 g of methyl 7-methoxy-3-oxo-3,4-dihydro-2H-1,5-benzoxathiepin-4-carboxylate, 1.96 g of 1-chloroacetyl 4-phenylpiperazine, 0.6 g of potassium iodide, 1.24 g of anhydrous potassium carbonate and 30 ml of methyl ethyl ketone is heated under reflux for 30 minutes with stirring. The inorganic substance is filtered off, and the filtrate is concentrated under reduced pressure. The resulting residue is dissolved in ethyl acetate, and the solution is washed with water and dried, followed by concentration by evaporation of the solvent under reduced pressure. The residue is purified by column chromatography on silica gel (eluent: hexane:ethyl acetate=2:1→1:1), followed by recrystallization from ethyl acetate-hexane to give 2.1 g of colorless crystals of methyl 7-methoxy-3-oxo-4-[2-oxo-2-(4-phenylpiperazin-1-yl)ethyl]-3,4-dihydro-2H-1,5-benzoxathiepin-4-carboxylate, m.p. of 146°–148° C.

IR spectrum (KBr) cm$^{-1}$: 1740, 1640

NMR spectrum (CDCl$_3$) δ: 4.78 ppm (2H, double doublet, C$_4$—CH$_2$CO—)

Elemental analysis, for $C_{24}H_{26}N_2O_6S$: Calcd.: C, 61.26; H, 5.57; N, 5.95, Found: C, 61.40; H, 5.60; N, 5.90.

REFERENCE EXAMPLES 10 to 19

By the same procedure as described in Reference Example 9, methyl 3-oxo-3,4-dihydro-2H-1,5-benzoxathiepin-4-carboxylate derivatives are allowed to undergo condensation with halides to give the compounds as shown in Table 1.

TABLE 1

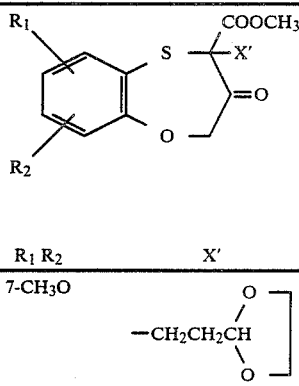

| Reference Example No. | R$_1$ R$_2$ | X' | Melting point (°C.) |
|---|---|---|---|
| 10 | 7-CH$_3$O | —CH$_2$CH$_2$CH(O—/O—) | 109–110 |
| 11 | 7-CH$_3$O | —CH$_2$CON(C$_2$H$_5$)$_2$ | Oily material |
| 12 | 7-CH$_3$O | —(CH$_2$)$_3$—Br | Oily material |
| 13 | 7-CH$_3$O | —(CH$_2$)$_4$—Br | Oily material |
| 14 | 7-CH$_3$O | —(CH$_2$)$_5$—Br | Oily material |
| 15 | 7-CH$_3$O | —(CH$_2$)$_6$—Br | Oily material |
| 16 | 7-CH$_3$O | —CH$_2$C$_6$H$_5$ | Oily material |
| 17 | 7-CH$_3$O | —CH$_3$ | Oily material |
| 18 | 7-CH$_3$O | —CH$_2$CO$_2$CH$_3$ | Oily material |

TABLE 1-continued (Structure: benzene ring with R₁, R₂ substituents, fused to S–CH(COOCH₃)–CH(X')–C(=O)–O ring)

| Reference Example No. | R₁ R₂ | X' | Melting point (°C.) |
|---|---|---|---|
| 19 | 7-CH₃O | –(CH₂)₄–N(phthalimide) | 78–81 |

REFERENCE EXAMPLE 20

In 15 ml of methanol is suspended 1.0 g of methyl 4-diethylcarbamoylmethyl-7-methoxy-3-oxo-3,4-dihydro-2H-1,5-benzoxathiepin-4-carboxylate as obtained in Reference Example 11, and 0.2 g of sodium borohydride is added portionwise to the suspension under ice-cooling with stirring. When the spot corresponding to the starting compound disappears on the TLC chromatogram, the reaction mixture is concentrated under reduced pressure, and water is added to the residue, followed by extraction with ethyl acetate. The organic layers are combined, washed with water and dried, and the solvent is evaporated off under reduced pressure. The resulting residue is separated and purified by column chromatography on silica gel (eluent: hexane-ethyl acetate=1:1), and from the first eluate is obtained 0.117 g of colorless needles of methyl trans-4-diethylcarbamoylmethyl-3-hydroxy-7-methoxy-3,4-dihydro-2H-1,5-benzoxathiepin-4-carboxylate, m.p. of 120°–123° C. (recrystallized from ethyl acetate-n-hexane).

Elemental analysis, for $C_{18}H_{25}NO_6S$: Calcd.: C, 56.38; H, 6.57; N, 3.65, Found: C, 56.50; H, 6.73; N, 3.61.

From the subsequent eluate, there is obtained 0.587 g of methyl cis-4-diethylcarbamoylmethyl-3-hydroxy-3,4-dihydro-2H-1,5-benzoxathiepin-4-carboxylate. Recrystallization from ethyl acetate-n-hexane yields colorless prisms, m.p. of 120°–122° C.

Elemental analysis, for $C_{18}H_{25}NO_6S$: Calcd.: C, 56.38; H, 6.57; N, 3.65, Found: C, 56.54; H, 6.71; N, 3.65.

REFERENCE EXAMPLE 21

By the same procedure as described in Reference Example 20, the compound as obtained in Reference Example 9 is subjected to reduction reaction with sodium borohydride to give two kinds of isomers, methyl cis- and trans-3-hydroxy-7-methoxy-4-[2-oxo-2-(4-phenylpiperazin-1-yl)ethyl]-3,4-dihydro-2H-1,5-benzoxathiepin-4-carboxylate. Cis isomer: Recrystallization from ethyl acetate yields colorless needles, m.p. of 213°–215° C. Mass spectrum m/e: 472 (M+), Elemental analysis, for $C_{24}H_{28}N_2O_6S$: Calcd.: C, 61.00; H, 5.97; N, 5.93, Found: C, 60.87; H, 5.84; N, 5.86.

Hydrochloride of transisomer: Recrystallization from methanol-ether yields colorless needles, m.p. of 170°–180° C. (decomp.)

Elemental analysis, for $C_{24}H_{28}N_2O_6S \cdot HCl \cdot \frac{1}{2}H_2O$: Calcd.: C, 55.64; H, 5.83; N, 5.40, Found: C, 55.38; H, 5.73; N, 5.44.

REFERENCE EXAMPLE 22

A 2.0 g quantity of methyl 4-(1,3-dioxolan-2-yl)ethyl-7-methoxy-3-oxo-3,4-dihydro-2H-1,5-benzoxathiepin-4-carboxylate as obtained in Reference Example 10, together with 2.0 g of lithium chloride, 0.3 ml of water and 20 ml of dimethylsulfoxide, is stirred at 100° C. for 5 hours. After the mixture is cooled, water is added to it, followed by extraction with ethyl acetate. The organic layers are combined, washed with water and dried, and the solvent is evaporated off. The resulting residue is purified by column chromatography on silica gel (eluent: hexane-ethyl acetate=2:1) to give a colorless oily material of 4-(1,3-dioxolan-2-yl)-ethyl-7-methoxy-3,4-dihydro-2H-1,5-benzoxathiepin-3-one.

IR spectrum (neat) cm⁻¹: 1730.

NMR spectrum (CDCl₃) δ: 1.6–2.3(4H, multiplet), 3.70 ppm (3H, singlet, OCH₃), 3.7–4.2(4H, multiplet), 4.60(2H, doublet), 4.6–5.0(2H, multiplet).

Mass spectrum m/e: 310 (M+).

REFERENCE EXAMPLE 23

By the same procedure as described in Reference Example 1, methyl 2-methoxycarbonylmethylthiophenoxyacetate is obtained from 2-mercaptophenol and methyl bromoacetate. Recrystallization from hexane-ethyl acetate yields colorless prisms, m.p. of 65°–66° C.

Elemental analysis, for $C_{12}H_{14}O_5S$: Calcd.: C, 53.32; H, 5.22, Found: C, 53.20; H, 5.29.

REFERENCE EXAMPLE 24

Methyl 2-methoxycarbonylmethylthiophenoxyacetate as obtained in Reference Example 23 is treated in the same manner as described in Reference Example 2 to give a colorless oily material of methyl 3-oxo-3,4-dihydro-2H-1,5-benzoxathiepin-4-carboxylate.

Elemental analysis, for $C_{11}H_{10}O_4S$: Calcd.: C, 55.45; H, 4.23, Found: C, 55.33; H, 4.41.

REFERENCE EXAMPLE 25

A mixture of 30 g of methyl 7-methoxy-3-oxo-3,4-dihydro-2H-1,5-benzoxathiepin-4-carboxylate, 50 g of 1-bromo-3-chloropropane, 46 g of anhydrous potassium carbonate, 10 g of potassium iodide, 1.0 g of tetrabutyl ammonium iodide and 300 ml of acetonitrile is heated under reflux for 4 hours. After the mixture is cooled, the inorganic substance is filtered off, and the filtrate is concentrated under reduced pressure. The resulting residue is dissolved in ethyl acetate, and the solution is washed with water and dried. The solvent is evaporated off under reduced pressure, and the residue is purified by column chromatography on silica gel (eluent: hexane:ethyl acetate:methylene chloride=10:1:10). Recrystallization from ethanol yields colorless prisms of methyl 4-(3-chloropropyl)-7-methoxy-3-oxo-3,4-dihydro-2H-1,5-benzoxathiepin-4-carboxylate. Yield of 17 g, m.p. of 64°–65° C.

Elemental analysis, for $C_{15}H_{17}ClO_5S$: Calcd.: C, 52.25; H, 4.97, Found: C, 52.33; H, 5.10.

REFERENCE EXAMPLE 26

In 200 ml of tetrahydrofuran is dissolved 17 g of methyl 4-(3-chloropropyl)-7-methoxy-3-oxo-3,4-dihydro-2H-1,5-benzoxathiepin-4-carboxylate, and 2.8 g of borane.trimethylamine complex and 12 g of boron trifluoride etherate are added to the solution, followed by stirring at room temperature for 20 hours. The reaction solution is concentrated under reduced pressure, and ice-cold water and dilute hydrochloric acid are added to the residue, followed by extraction with ethyl acetate. The organic layer is washed with water and dried, and the solvent is evaporated off under reduced pressure. The resulting residue is purified by column chromatography on silica gel (eluent: hexane:ethyl acetate=1:1) to give 13 g of a colorless oily material of methyl cis-4-(3-chloropropyl)-3-hydroxy-7-methoxy-3,4-dihydro-2H-1,5-benzoxathiepin-4-carboxylate.

Elemental analysis, for $C_{15}H_{19}ClO_5S$: Calcd.: C, 51.95; H, 5.52, Found: C, 52.08; H, 5.48.

Mass spectrum m/e: 346, 348(M+)

REFERENCE EXAMPLE 27

2-Mercapto-4-methylphenol is treated with methyl bromoacetate in the same manner as described in Reference Example 1 to give methyl 2-methoxycarbonylmethylthio-4-methylphenoxyacetate as colorless prisms (recrystallized from methanol).

mp. 45°–46° C.

Elemental Analysis for $C_{13}H_{16}O_5S$: Calcd.: C, 54.92; H, 5.67, Found: C, 55.10; H, 5.70.

REFERENCE EXAMPLE 28

4-Chloro-2-mercaptophenol is treated with methyl bromoacetate in the same manner as described in Reference Example 1 to give methyl 4-chloro-2-methoxycarbonylmethylthiophenoxyacetate as colorless prisms (recrystallized from ethyl acetate-hexane).

mp. 76°–77° C.

Elemental Analysis for $C_{12}H_{13}ClO_5S$: Calcd.: C, 47.30; H, 4.30, Found: C, 47.40; H, 4.29.

REFERENCE EXAMPLE 29

Methyl 2-methoxycarbonylmethylthio-4-methylphenoxyacetate (8.9 g) is treated with sodium methoxide in the same manner as described in Reference Example 2 to give methyl 7-methyl-3-oxo-3,4-dihydro-2H-1,5-benzoxathiepin-4-carboxylate (5.8 g) as a colorless oil.

Mass spectrum (m/e): 252(M+).

IR $\nu_{max}^{neat}$ cm$^{-1}$: 1730–1750(C=O)

NMR (CDCl$_3$) δ: 2.22(3H, s, C$_7$—CH$_3$), 3.80(3H, s, COOCH$_3$), 4.62(2H, double doublet, C$_2$—H), 4.80(1H, s, C$_4$—H).

REFERENCE EXAMPLE 30

Methyl 4-chloro-2-methoxycarbonylmethylthiophenoxyacetate is treated with sodium methoxide in the same manner as described in Reference Example 2 to give methyl 7-chloro-3-oxo-3,4-dihydro-2H-1,5-benzoxathiepin-4-carboxylate as colorless needles, mp. 92°–94° C.

Elemental Analysis for $C_{11}H_9ClO_4S$: Calcd.: C, 48.45; H, 3.33, Found: C, 48.45; H, 3.06.

REFERENCE EXAMPLE 31

Methyl 7-methyl-3-oxo-3,4-dihydro-2H-1,5-benzoxathiepin-4-carboxylate (4.1 g) is treated with 1-bromo-3-chloropropane in the same manner as described in Reference Example 25 to give methyl 4-(3-chloropropyl)-7-methyl-3-oxo-3,4-dihydro-2H-1,5-benzoxathiepin-4-carboxylate (2.0 g) as a colorless oil.

Mass spectrum (m/e): 328, 330(M+).

IR $\nu_{max}^{neat}$ cm$^{-1}$: 1760, 1730(C=O).

NMR (CDCl$_3$) δ: 2.20(3H, s, C$_7$—CH$_3$), 3.70(3H, s, CO$_2$CH$_3$), 4.62(2H, double doublet, C$_2$—H).

REFERENCE EXAMPLE 32

Methyl 4-(3-chloropropyl)-7-methyl-3-oxo-3,4-dihydro-2H-1,5-benzoxathiepin-4-carboxylate 2.0 g is reduced by sodium borohydride in the same manner as described in Reference Example 20 to give Methyl cis- and trans-4-(3-chloropropyl)-3-hydroxy-7-methyl-3,4-dihydro-2H-1,5-benzoxathiepin-4-carboxylate.

cis-isomer (1.2 g, colorless oil)

IR $\nu_{max}^{neat}$ cm$^{-1}$: 3520(OH), 1730(C=O).

NMR (CDCl$_3$) δ: 2.28 ppm(3H, s, C$_7$—CH$_3$), 3.78 ppm(3H, s, CO$_2$CH$_3$).

trans-isomer (0.7 g, colorless oil),

IR $\nu_{max}^{neat}$ cm$^{-1}$: 3540(OH), 1720(C=O),

NMR (CDCl$_3$) δ: 2.24 ppm(3H, s, C$_7$—CH$_3$), 3.55 ppm(3H, s, CO$_2$CH$_3$).

REFERENCE EXAMPLE 33

Methyl 7-chloro-3-oxo-3,4-dihydro-2H-1,5-benzoxathiepin-4-carboxylate is treated with 1-bromo-3-chloropropane in the same manner as described in Reference Example 25 to give methyl 7-chloro-4-(3-chloropropyl)-3-oxo-3,4-dihydro-2H-1,5-benzoxathiepin-4-carboxylate as a colorless oil.

IR $\nu_{max}^{neat}$ cm$^{-1}$: 1760, 1730(C=O).

NMR (CDCl$_3$) δ: 3.68 ppm(3H, s, CO$_2$CH$_3$), 4.62 ppm(2H, double doublet, C$_2$—H).

REFERENCE EXAMPLE 34

Methyl 7-chloro-4-(3-chloropropyl)-3-oxo-3,4-dihydro-2H-1,5-benzoxathiepin-4-carboxylate is reduced by sodium borohydride in the same manner as described in Reference Example 20 to give methyl cis- and trans-7-chloro-4-(3-chloropropyl)-3-hydroxy-3,4-dihydro-2H-1,5-benzoxathiepin-4-carboxylate.

cis-isomer (colorless oil)

IR $\nu_{max}^{neat}$ cm$^{-1}$: 3520(OH), 1730(C=O).

NMR (CDCl$_3$) δ: 3.80 ppm(3H, s, CO$_2$CH$_3$).

trans-isomer (colorless oil)

IR $\nu_{max}^{neat}$ cm$^{-1}$: 3520(OH), 1720(C=O).

NMR (CDCl$_3$) δ: 3.60 ppm(3H, s, CO$_2$CH$_3$).

REFERENCE EXAMPLE 35

A mixture of methyl 4-(3-chloropropyl)-7-methoxy-3-oxo-3,4-dihydro-2H-1,5-benzoxathiepin-4-carboxylate (5.0 g) obtained in Reference Example 25, dimethylsulfoxide (30 ml), water (0.3 ml) and lithium chloride (1.5 g) is heated at 100° C. for 5 hours with stirring. The reaction mixture is poured into ice-water and extracted with ethyl acetate. The organic layer is washed with water, dried over anhydrous sodium sulfate and evaporated to dryness in vacuo. The residue is submited to column chromatography on silica gel eluting with hexane-ethyl acetate (2:1) to give 4-(3-chloropropyl)-7-methoxy-3,4-dihydro-2H-1,5-benzoxathiepin-3-one (2.0 g) as a colorless oil.

Elemental Analysis for $C_{13}H_{15}ClO_3S$: Calcd.: C, 54.45; H, 5.27, Found: C, 54.60; H, 5.24.

Mass spectrum (m/e): 286, 288(M+).

REFERENCE EXAMPLE 36

To a solution of 4-(3-chloropropyl)-7-methoxy-3,4-dihydro-2H-1,5-benzoxathiepin-3-one (0.8 g) in tetrahydrofuran (2 ml) and methanol (10 ml) is added sodium borohydride (0.1 g) under ice-cooling. The reaction mixture is stirred for another one hour and evaporated in vacuo. The residue is mixed with ethyl acetate and water. The organic layer is separated, washed with water, dried over anhydrous sodium sulfate and evaporated to dryness in vacuo. The residue is submited to column chromatography on silica gel eluting with ethyl acetate-hexane (1:1) to give 4-(3-chloropropyl)-7-methoxy-3,4-dihydro-2H-1,5-benzoxathiepin-3-ol (0.68 g) as a colorless oil.

Elemental Analysis for $C_{13}H_{17}ClO_3S$: Calcd.: C, 54.03; H, 5.93, Found: C, 54.37; H, 6.13.

REFERENCE EXAMPLE 37

To a solution of methyl cis-4-(3-chloropropyl)-3-hydroxy-7-methoxy-3,4-dihydro-2H-1,5-benzoxathiepin-4-carboxylate (3.5 g) in methanol (50 ml) is added a solution of 1N NaOH (10 ml) and stirred for 15 hours. The reaction mixture is evaporated in vacuo. After addition of water 50 ml to the residue, the mixture is washed with ethyl ether. The aqueous layer is acidified with dil.HCl solution and extracted with ethyl acetate. The organic layer is washed with water, dried over anhydrous $Na_2SO_4$ and evaporated to dryness in vacuo. The residue is recrystallized from hexane-AcOEt to give cis-4-(3-chloropropyl)-3-hydroxy-7-methoxy-3,4-dihydro-2H-1,5-benzoxathiepin-4-carboxylic acid (2.1 g) as colorless prisms, mp. 175°–178° C.

Elemental Analysis for $C_{14}H_{17}O_5SCl$: Calcd.: C, 50.53; H, 5.15, Found: C, 50.69; H, 5.07.

REFERENCE EXAMPLE 38

To a solution of cis-4-(3-chloropropyl)-3-hydroxy-7-methoxy-3,4-dihydro-2H-1,5-benzoxathiepin-4-carboxylic acid (1.0 g) in pyridine (5 ml) is added acetic anhydride (4 ml), and allowed to stand at room temperature for 5 hours. The reaction mixture is poured into water and extracted with ethyl acetate. The organic layer is washed with water, dried over anhydrous $Na_2SO_4$ and evaporated to dryness in vacuo. The residue is recrystallized from AcOEt-hexane to give cis-3-acetoxy-4-(3-chloropropyl)-7-methoxy-3,4-dihydro-2H-1,5-benzoxathiepin-4-carboxylic acid (0.95 g) as colorless prisms, mp 163°–165° C.

Elemental Analysis for $C_{16}H_{19}O_6SCl$: Calcd.: C, 51.27; H, 5.11, Found: C, 51.44; H, 5.17.

REFERENCE EXAMPLE 39

To a mixture of cis-3-acetoxy-4-(3-chloropropyl)-7-methoxy-3,4-dihydro-2H-1,5-benzoxathiepin-4-carboxylic acid (0.8 g), benzylamine (0.27 g) and N,N-dimethylformamide (6 ml) is added diethyl phosphorocyanidate (0.52 g) and then triethylamine (0.45 ml) under ice-cooling with stirring. The reaction mixture is stirred under ice-cooling for 10 minutes and at room temperature for further 3 hours and then poured into ice-water. The crystalline deposit is collected by filtration, washed with water, and then with ethyl acetate and dried to give cis-3-acetoxy-4-(3-chloropropyl)-7-methoxy-3,4-dihydro-2H-1,5-benzoxathiepin-4-N-benzylcarboxamide (0.57 g) which is isolated as colorless plates, mp 224°–226° C. (from ethyl acetate).

Mass spectrum m/e: 463, 465(M+)

Elemental Analysis for $C_{23}H_{26}NO_5SCl$: Calcd.: C, 59.54; H, 5.65; N, 3.02, Found: C, 59.81; H, 5.48; N, 2.82.

REFERENCE EXAMPLE 40

2-Mercapto-5-methoxyphenol is treated in the same manner as described in Reference Example 1 to give methyl 5-methoxy-2-methoxycarbonylmethylthiophenoxyacetate as a colorless oil.

Mass spectrum (m/e): 300(M+),

IR spectrum $\nu_{max}^{neat}$ cm$^{-1}$: 1740 (ester).

REFERENCE EXAMPLE 41

Methyl 5-methoxy-2-methoxycarbonylmethylthiophenoxyacetate is treated in the same manner as described in Reference Example 2 to give methyl 8-methoxy-3-oxo-3,4-dihydro-2H-1,5-benzoxathiepin-4-carboxylate as a pale yellow oil.

Mass spectrum (m/e): 268(M+).

NMR spectrum (CDCl$_3$) δ: 3.72(3H, singlet), 3.78(3H, singlet), 4.76(2H, double doublet, J=18 Hz), 4.80(1H, singlet).

REFERENCE EXAMPLE 42

Methyl 8-methoxy-3-oxo-3,4-dihydro-2H-1,5-benzoxathiepin-4-carboxylate is treated in the same manner as described in Reference Example 25 to give methyl 4-(3-chloropropyl)-3-oxo-8-methoxy-3,4-dihydro-2H-1,5-benzoxathiepin-4-carboxylate as a colorless oil.

Mass spectrum (m/e): 344, 346(M+).

IR spectrum $\nu_{max}^{neat}$ cm$^{-1}$: 1755, 1720.

REFERENCE EXAMPLE 43

Methyl 4-(3-chloropropyl)-3-oxo-8-methoxy-3,4-dihydro-2H-1,5-benzoxathiepin-4-carboxylate is treated with sodium borohydride in the same manner as described in Reference Example 20 to give methyl cis- and trans-3-hydroxy-4-(3-chloropropyl)-8-methoxy-3,4-dihydro-2H-1,5-benzoxathiepin-4-carboxylate. cis-Isomer (colorless oil):

Mass spectrum (m/e): 346, 348(M+)

IR spectrum $\nu_{max}^{neat}$ cm$^{-1}$: 3520(OH), 1735(C=O), trans-Isomer (colorless oil):

Mass spectrum (m/e): 346, 348(M+),

IR spectrum $\nu_{max}^{neat}$ cm$^{-1}$: 3500(OH), 1720(C=O).

REFERENCE EXAMPLE 44

4-Benzyloxy-2-mercaptophenol is treated in the same manner as described in Reference Example 1 to give methyl 4-benzyloxy-2-methoxycarbonylmethylthiophenoxyacetate as colorless prisms.
Melting point: 52°–53° C.
Elemental Analysis for $C_{19}H_{20}O_6S$: Calcd.: C, 60.63; H, 5.36, Found: C, 60.75; H, 5.39.

REFERENCE EXAMPLE 45

Methyl 4-benzyloxy-2-methoxycarbonylmethylthiophenoxyacetate is treated in the same manner as describe in Reference Example 2 to give methyl 7-benzyloxy-3-oxo-3,4-dihydro-2H-1,5-benzoxathiepin-4-carboxylate as colorless prisms. Melting point: 101°–102° C.
Elemental Analysis for $C_{18}H_{16}O_5S$: Calcd.: C, 62.78; H, 4.68, Found: C, 62.71; H, 4.38.

REFERENCE EXAMPLE 46

Methyl 7-benzyloxy-3-oxo-3,4-dihydro-2H-1,5-benzoxathiepin-4-carboxylate is treated in the same manner as described in Reference Example 25 to give methyl 7-benzyloxy-4-(3-chloropropyl)-3-oxo-3,4-dihydro-2H-1,5-benzoxathiepin-4-carboxylate as a colorless oil.
IR spectrum $\nu_{max}^{neat}$ cm$^{-1}$: 1755, 1725.
NMR spectrum (CDCl$_3$) δ: 3.72(3H, singlet), 4.60 (2H, double doublet).

REFERENCE EXAMPLE 47

Methyl 7-benzyloxy-4-(3-chloropropyl)-3-oxo-3,4-dihydro-2H,1,5-benzoxathiepin-4-carboxylate is treated in the same manner as described in Reference Example 20 to give methyl cis-7-benzyloxy-4-(3-chloropropyl)-3-hydroxy-3,4-dihydro-2H-1,5-benzoxathiepin-4-carboxylate as a colorless oil
IR spectrum $\nu_{max}^{neat}$ cm$^{-1}$: 3550(OH), 1740(ester).

REFERENCE EXAMPLE 48

Methyl 7-benzyloxy-4-(3-chloropropyl)-3-hydroxy-3,4-dihydro-2H-1,5-benzoxathiepin-4-carboxylate is treated in the same manner as described in the belowmentioned Example 39 to give methyl cis-7-benzyloxy-3-hydroxy-4-[3-(4-phenylpiperazin-1-yl)propyl]-3,4-dihydro-2H-1,5-benzoxathiepin-4-carboxylate dihydrochloride as an amorphous powder.
Elemental Analysis for $C_{31}H_{36}N_2O_5S \cdot 2HCl$: Calcd.: C, 59.90; H, 6.16; N, 4.51, Found: C, 59.87; H, 6.32; N, 4.63.

REFERENCE EXAMPLE 49

A mixture of 3.0 g of methyl cis-7-benzyloxy-4-(3-chloropropyl)-3-hydroxy-3,4-dihydro-2H-1,5-benzoxathiepin-4-carboxylate, 1.9 g of N-4-hydroxyphenylpiperazine and 5 ml of N,N-dimethylacetamide is stirred at 90° C. for 6 hours. Water is added to the mixture and the mixture is extracted with ethyl acetate. The organic layers are combined, washed with water and dried and the solvent is evaporated off under reduced pressure. The residue is purified by silica gel column chromatography [eluent: haxane-ethyl acetate-methanol (70:150:6)] to give 2.3 g of methyl cis-7-benzyloxy-3-hydroxy-4-[3-[4-(4-hydroxyphenol)piperazin-1-yl]propyl]-3,4-dihydro-2H-1,5-benzoxathiepin-4-carboxylate as a pale yellow oil. The product is converted to a powder of the hydrochloride.
Elemental Analysis for $C_{31}H_{36}N_2O_6S \cdot HCl$: Calcd.: C, 61.93; H, 6.20; N, 4.66, Found: C, 61.91; H, 6.01; N, 4.65.

EXAMPLE 1

A mixture of 10 g of methyl 7-methoxy-3-oxo-3,4-dihydro-2H-1,5-benzoxathiepin-4-carboxylate, 9.8 g of 3-(4-phenylpiperazin-1-yl)propyl chloride, 6.2 g of anhydrous potassium carbonate, 3.0 g of potassium iodide and 150 ml of methyl ethyl ketone is stirred with heating under reflux for 25 hours. After the mixture is cooled, the inorganic substance is filtered off, and the filtrate is concentrated under reduced pressure. The resulting residue is dissolved in ethyl acetate, and the solution is washed with water and dried. The solvent is evaporated off under reduced pressure, and the resulting residue is purified by column chromatography on silica gel (eluent: hexane:ethyl acetate=3:1) to give methyl 7-methoxy-3-oxo-4-[3-(4-phenylpiperazin-1-yl)propyl]-3,4-dihydro-2H-1,5-benzoxathiepin-4-carboxylate. Recrystallization from methanol gives white crystals.
m.p. of 110°–112° C. Yield of 2.1 g.
Elemental analysis, for $C_{25}H_{30}N_2O_5S$: Calcd.: C, 63.81; H, 6.43; N, 5.95, Found: C, 63.50; H, 6.37; N, 5.71.

EXAMPLES 2 TO 3

By the same procedure as described in Example 1, the compounds as shown in Table 2 are obtained by the reaction of methyl 7-methoxy-3-oxo-3,4-dihydro-2H-1,5-benzoxathiepin-4-carboxylate with an alkyl halide.

TABLE 2

| Example No. | R$_1$, R$_2$ | X' | Elemental analysis (hydrochloride) (Parenthesized figures are calculated values) | | |
|---|---|---|---|---|---|
| | | | C | H | N |
| | | | White powder as ¾ hydrate. | | |
| 2 | 7-CH$_3$O | –(CH$_2$)$_3$–N(piperazinyl-phenyl) | 60.20 (60.10) | 6.30 (6.50) | 2.57 (2.70) |
| | | | White powder as 1½ hydrate | | |

TABLE 2-continued

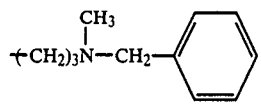

| Example No. | $R_1, R_2$ | X' | C | H | N |
|---|---|---|---|---|---|
| | | | Elemental analysis (hydrochloride) (Parenthesized figures are calculated values) | | |
| 3 | 7-CH$_3$O | -(CH$_2$)$_3$N(CH$_3$)-CH$_2$-C$_6$H$_5$ | 56.03 (56.25) | 6.34 (6.25) | 2.84 (2.90) |

EXAMPLE 4

A mixture of 1.7 g of methyl 4-(4-bromobutyl)-7-methoxy-3-oxo-3,4-dihydro-2H-1,5-benzoxathiepin-4-carboxylate as obtained in Reference Example 13, 1.37 g of N-phenylpiperazine, 0.7 g of potassium iodide, 1.2 g of anhydrous potassium carbonate and 30 ml of acetonitrile is stirred with heating under reflux for 1.5 hours. After the mixture is cooled, the inorganic substance is filtered off, and the filtrate is concentrated under reduced pressure. Water is added to the residue, and the mixture is extracted with ethyl acetate. The organic layers are combined, washed with water and dried, and the solvent is evaporated off under reduced pressure. The residue is purified by column chromatography on silica gel (eluent: hexane-ethyl acetate=2:1) to give 1.0 g of a colorless oily material of methyl 7-methoxy-3-oxo-4-[4-(4-phenylpiperazin-1-yl)butyl]-3,4-dihydro-2H-1,5-benzoxathiepin-4-carboxylate. Hydrochloride, white crystals, m.p. of 155°–165° C. (decomp).

Elemental analysis, for C$_{26}$H$_{32}$N$_2$O$_5$S.2HCl.$\frac{1}{2}$H$_2$O: Calcd.: C, 55.12; H, 6.22; N, 4.95, Found: C, 55.30; H, 6.19; N, 4.96.

EXAMPLES 5 TO 11

By the same procedure as described in Example 4, the compounds as shown in Table 3 are obtained by the substitution reaction of the halides obtained in Reference Examples 12 to 15 with amines.

TABLE 3

| Ex. No. | $R_1, R_2$ | X' | Hydrochloride Melting Point (°C.) | Elemental Analysis for hydrochloride (parenthesized figures are calculated values) | | | Mass spectrum m/e |
|---|---|---|---|---|---|---|---|
| | | | | C | H | N | |
| 5 | 7-CH$_3$O | -(CH$_2$)$_3$-N(piperazine)-C$_6$H$_5$ | 130–150 (decomp.) | 2HCl.$\frac{1}{2}$H$_2$O 56.00 (55.85) | 6.41 (6.42) | 4.81 (4.83) | |
| 6 | 7-CH$_3$O | -(CH$_2$)$_5$-N(piperazine)-C$_6$H$_5$ | powder | 2HCl 57.26 (57.42) | 6.70 (6.54) | 4.74 (4.79) | |
| 7 | 7-CH$_3$O | -(CH$_2$)$_3$-N(piperazine)-N-CH(C$_6$H$_5$)$_2$ | oil (free base) | | | | 560(M$^+$) |

TABLE 3-continued

[Structure: benzene ring with R1, R2 substituents, fused with S-CH(CO2CH3)-X' and O-CH(=O) forming a benzoxathiepin core]

| Ex. No. | R1, R2 | X' | Hydrochloride Melting Point (°C.) | Elemental Analysis for hydrochloride (parenthesized figures are calculated values) C / H / N | Mass spectrum m/e |
|---|---|---|---|---|---|
| 8 | 7-CH3O | —(CH2)3—N(piperazine)N—(3-Cl-phenyl) | oil (free base) | | 504, 506 (M+) |
| 9 | 7-CH3O | —(CH2)3—N(piperazine)N—(2-OCH3-phenyl) | oil (free base) | | 500(M+) |
| 10 | 7-CH3O | —(CH2)3—N(piperazine)N—(2-pyridyl) | oil (free base) | | 471(M+) |
| 11 | 7-CH3O | —(CH2)3—N(CH3)—CH2CH2—(3,4-diOCH3-phenyl) | oil (free base) | | 503(M+) |

EXAMPLE 12

In a solvent mixture of 40 ml of tetrahydrofuran and 200 ml of methanol is dissolved 38 g of methyl 7-methoxy-3-oxo-4-[3-(4-phenylpiperazin-1-yl)propyl]-3,4-dihydro-2H-1,5-benzoxathiepin-4-carboxylate as obtained in Example 1, and 3.7 g of sodium borohydride is added portionwise to the solution under ice-cooling with stirring. After the completion of reaction, the solvent is evaporated off under reduced pressure, and water is added to the residue, followed by extraction with ethyl acetate. The organic layers are combined, washed with water and dried, and the solvent is evaporated off under reduced pressure. The resulting residue is separated and purified by column chromatography on silica gel (eluent: hexane-ethyl acetate-methanol=20:10:1). From the first eluate there is obtained 12 g of a colorless oily material of methyl trans-3-hydroxy-7-methoxy-4-[3-(4-phenylpiperazin-1-yl)propyl]-3,4-dihydro-2H-1,5-benzoxathiepin-4-carboxylate.

IR spectrum (neat) cm$^{-1}$: 3520, 1720.

NMR spectrum (CDCl3) δ: 3.45(3H, singlet, OCH3), 3.60(3H, singlet, OCH3).

The compound turns into a white powder as the hydrochloride salt.

Elemental analysis, for $C_{25}H_{32}N_2O_5S \cdot 2HCl \cdot \frac{1}{2}H_2O$: Calcd: C, 54.15; H, 6.36; N, 5.05, Found: C, 54.27; H, 6.20; N, 4.89.

From the subsequent eluate, there is obtaind 18 g of a colorless oily material of methyl cis-3-hydroxy-7-methoxy4-[3-(4-phenylpiperazin-1-yl)propyl]-3,4-dihydro-2H-1,5-benzoxathiepin-4-carboxylate.

IR spectrum (neat) cm$^{-1}$: 3530, 1740.

NMR spectrum (CDCl3) δ: 3.60(3H, singlet, OCH3), 3.62 (3H, singlet, OCH3).

As the hydrochloride salt, m.p. of 165°–175° C. (decomp.).

Elemental analysis, for $C_{25}H_{32}N_2O_5S \cdot 2HCl \cdot \frac{1}{2}H_2O$: Calcd.: C, 54.15; H, 6.36; N, 5.05 Found: C, 54.02; H, 6.33; N, 5.00

EXAMPLES 13 to 22

By the same procedure as described in Example 12, the compounds as obtained in Examples 2 to 11 are subjected to reduction reaction with sodium borohydride to give the compounds as shown in Table 4.

TABLE 4

Configuration shows relationship between OH (3rd position) and $CO_2CH_3$ (4th position)

| Ex. No. | $R_1, R_2$ | X' | configuration | Hydrochloride Melting Point (°C.) | Elemental Analysis for hydrochloride (parenthesized figures are calculated values) C / H / N |
|---|---|---|---|---|---|
| 13 | 7-$OCH_3$ | $-(CH_2)_3-N$(piperidine-4-phenyl) | cis + trans | Powder | $C_{26}H_{33}NO_5S \cdot HCl \cdot \frac{1}{2}H_2O$<br>60.47  6.89  2.64<br>(60.39) (6.82) (2.71) |
| 14 | 7-$OCH_3$ | $-(CH_2)_3-N(CH_3)-CH_2-$phenyl | cis + trans | Powder | $C_{23}H_{29}NO_5S \cdot HCl \cdot \frac{3}{4}H_2O$<br>57.44  6.69  2.71<br>(57.37) (6.59) (2.91) |
| 15a | 7-$OCH_3$ | $-(CH_2)_4-N(piperazine)-N-phenyl$ | cis | Powder | $C_{26}H_{34}N_2O_5S \cdot 2HCl \cdot \frac{1}{4}H_2O$<br>55.30  6.41  4.94<br>(55.36) (6.52) (4.97) |
| 15b | 7-$OCH_3$ | $-(CH_2)_4-N(piperazine)-N-phenyl$ | trans | Carbonate 128–130 | $C_{26}H_{34}N_2O_5S \cdot H_2CO_3$<br>58.97  6.75  5.28<br>(59.10) (6.61) (5.11) |
| 16 | 7-$OCH_3$ | $-(CH_2)_5-N(piperazine)-N-phenyl$ | cis | Powder | $C_{27}H_{36}N_2O_5S \cdot 2HCl \cdot H_2O$<br>54.81  6.81  4.73<br>(54.49) (6.95) (4.85) |
| 17 | 7-$OCH_3$ | $-(CH_2)_6-N(piperazine)-N-phenyl$ | cis + trans | 165–175 (free base 112–114) | $C_{28}H_{38}N_2O_5S$ (free base)<br>65.23  7.54  5.27<br>(65.34) (7.44) (5.44) |
| 18a | 7-$OCH_3$ | $-(CH_2)_3-N(piperazine)-N-CH(phenyl)_2$ | cis | (free base 133–135) | $C_{32}H_{38}N_2O_5S$ (free base)<br>68.48  6.73  4.97<br>(68.30) (6.81) (4.98) |
| 18b | 7-$OCH_3$ | $-(CH_2)_3-N(piperazine)-N-CH(phenyl)_2$ | trans | (free base 173–176) | $C_{32}H_{38}N_2O_5S$ (free base)<br>68.34  6.81  4.82<br>(68.30) (6.81) (4.98) |
| 19a | 7-$CH_3O$ | $-(CH_2)_3-N(piperazine)-N-(3-chlorophenyl)$ | cis | 140–150 | $C_{25}H_{31}N_2O_5SCl \cdot 2HCl \cdot \frac{3}{4}H_2O$<br>50.64  6.11  4.61<br>(50.59) (5.85) (4.72) |

TABLE 4-continued

[Structure: benzoxathiepin with R1, R2 on benzene ring, S, O, CO2CH3, X', OH substituents]

| Ex. No. | R₁, R₂ | X' | configuration | Hydrochloride Melting Point (°C.) | Elemental Analysis for hydrochloride (parenthesized figures are calculated values) C | H | N |
|---|---|---|---|---|---|---|---|
| 19b | 7-CH₃O | –(CH₂)₃N(piperazine)N-(2-Cl-phenyl) | trans | (free base 112–113) | $C_{25}H_{31}N_2O_5SCl$ (free base) 59.28 (59.22) | 6.27 (6.16) | 5.34 (5.52) |
| 20a | 7-CH₃O | –(CH₂)₃N(piperazine)N-(2-OCH₃-phenyl) | cis | Powder | $C_{26}H_{34}N_2O_6S \cdot 2HCl \cdot 1\frac{1}{2}H_2O$ 51.99 (51.83) | 6.55 (6.52) | 4.39 (4.65) |
| 20b | 7-CH₃O | –(CH₂)₃N(piperazine)N-(2-OCH₃-phenyl) | trans | Powder | $C_{26}H_{34}N_2O_6S \cdot 2HCl \cdot H_2O$ 52.51 (52.61) | 6.62 (6.45) | 4.83 (4.72) |
| 21a | 7-CH₃O | –(CH₂)₃N(piperazine)N-(2-pyridyl) | cis | Powder | $C_{24}H_{31}N_3O_5S \cdot 2HCl \cdot 7/4H_2O$ 49.97 (49.86) | 6.66 (6.36) | 7.06 (7.26) |
| 21b | 7-CH₃O | –(CH₂)₃N(piperazine)N-(2-pyridyl) | trans | Powder | $C_{24}H_{31}N_3O_5S \cdot 2HCl \cdot \frac{1}{2}H_2O$ 51.75 (51.89) | 5.97 (6.20) | 7.54 (7.56) |
| 22 | 7-CH₃O | –(CH₂)₃N(CH₃)–CH₂CH₂–(3,4-dimethoxyphenyl) | cis + trans | Powder | $C_{26}H_{35}NO_7S \cdot HCl \cdot H_2O$ 56.01 (55.76) | 6.82 (6.84) | 2.30 (2.50) |

EXAMPLE 23

To a tetrahydrofuran solution of sodium monoacetoxyborohydride prepared by suspending 0.1 g of sodium borohydride in 15 ml of tetrahydrofuran and by adding 0.19 g of acetic acid dropwise to the suspension with stirring is added 0.5 g of methyl cis-3-hydroxy-7-methoxy-4-[2-oxo-2-(4-phenylpiperazin-1-yl)ethyl]-3,4-dihydro-2H-1,5-benzoxathiepin-4-carboxylate as obtained in Reference Example 21, followed by heating under reflux for 20 hours. The reaction solution is concentrated under reduced pressure, and water is added to the residue, followed by extraction with ethyl acetate. The organic layer is washed with water and dried, and the solvent is evaporated off under reduced pressure. The residue is purified by silica-gel column chromatography (eluent: hexane-ethyl acetate=1:1) to give 0.2 g of a colorless oily material of methyl cis-3-hydroxy-7-methoxy-4-[2-(4-phenylpiperazin1-yl)ethyl]-3,4-dihydro-2H-1,5-benzoxathiepin-4-carboxylate, which turns into a white powder as the hydrochloride salt.

Elemental analysis, for $C_{24}H_{30}N_2O_5S \cdot 2HCl \cdot \frac{1}{4}H_2O$ Calcd.: C, 53.77; H, 6.11; N, 5.23; Found: C, 53.67; H, 6.19; N, 5.35.

EXAMPLE 24

To a mixture of 0.24 g of lithium aluminum hydride and 50 ml of ethyl ether is added 0.7 g of methyl cis-3-hydroxy-7-methoxy-4-[2-oxo-2-(4-phenylpiperazin-1-yl)ethyl]-3,4-dihydro-2H-1,5-benzoxathiepin-4-carboxylate as obtained in Reference Example 21, followed by heating under reflux for 2 hours. After the reaction mixture is cooled, 0.25 ml of water, 0.25 ml of a 15% aqueous sodium hydroxide solution and 0.75 ml of water are added to it in the mentioned order, followed by stirring for 30 minutes. The precipitate is filtered off and washed with ethyl acetate, and the filtrate and washings are combined and concentrated under reduced pressure. The residue is recrystallized from ethyl acetate to give 0.5 g of colorless prisms of cis-4-hydroxymethyl-7-methoxy-4-[2-(4-phenylpiperazin-1-yl)ethyl]-3,4-dihydro-2H-1,5-benzoxathiepin-3-ol, m.p. of 153°–156° C.

Elemental analysis, for $C_{23}H_{30}N_2O_4S$: Calcd.: C, 64.16; H, 7.02; N, 6.51; Found: C, 64.30; H, 7.10; N, 6.48.

EXAMPLE 25

Methyl cis-4-diethylcarbamoylmethyl-3-hydroxy-3,4-dihydro-2H-1,5-benzoxathiepin-4-carboxylate as obtained in Reference Example 20 is treated in the same manner as described in Example 24 to give a colorless oily material of cis-4-(2-diethylaminoethyl)-4-hydroxymethyl-7-methoxy3,4-dihydro-2H-1,5-benzoxathiepin-3-ol.

IR spectrum (neat) cm$^{-1}$: 3400.

NMR spectrum (CDCl$_3$) δ: 1.00 ppm(6H, triplet, 2CH$_3$), 1.75 (2H, m), 2.45 (6H, m), 3.58 (3H, singlet, OCH$_3$), 3.60 (2H, double doublet, CH$_2$OH), 3.90 (2H, singlet,

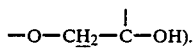

).

EXAMPLE 26

In 20 ml of methanol is dissolved 0.8 g of 4-(1,3-dioxaolan-1-yl)ethyl-7-methoxy-3,4-dihydro-2H-1,5-benzoxathiepin-3-one as obtained in Reference Example 22, and sodium borohydride is added portionwise to the solution with stirring. At the time when the spot corresponding to the starting compound disappears on the thin-layer chromatogram, a solution of 1N aqueous sodium hydroxide is added to the reaction solution, followed by extraction with ethyl acetate. The organic layers are combined, washed with water and dried, and the solvent is evaporated off under reduced pressure. 5 ml of dioxane, 2 ml of water and 40 mg of p-toluenesulfonic acid are added to the residue, and the mixture is stirred at room temperature for 8 hours. Water is added to the reaction solution, followed by extraction with ethyl acetate. The organic layers are combined, and the solvent is evaporated off under reduced pressure. 10 ml of acetonitrile and 400 ml of 4-phenylpiperazine are added to the residue thus obtained, followed by stirring at room temperature for 20 hours. 200 mg of sodium cyanoborohydride and 5 ml of methanol are added to the mixture, followed by stirring for further 10 hours. Sodium hydroxide (1N) is added to the reaction solution, followed by extraction with ethyl acetate. The organic layers are combined, washed with water and dried, and the solvent is evaporated off under reduced pressure. The resulting residue is separated and purified by silica-gel column chromatography (eluent: hexane-ethyl acetate-methanol=10:10:1) to give 200 mg of a colorless oily material of 7-methoxy-4-[3-(4-phenylpiperazin-1-yl)propyl]-3,4-dihydro-2H-1,5-benzoxathiepin-3-ol, which turns into a white powder as the hydrochloride salt.

Elemental analysis, for $C_{23}H_{30}N_2O_3S.2HCl.\frac{1}{2}H_2O$: Calcd.: C, 55.63; H, 6.70; N, 5.64; Found: C, 55.73; H, 6.61; N, 5.64.

EXAMPLE 27

In 10 ml of pyridine is dissolved 0.7 g of cis-4-(2-diethylaminoethyl)-4-hydroxymethyl-7-methoxy-3,4-dihydro-2H-1,5-benzoxathiepin-3-ol as obtained in Example 25, and 6 ml of acetic anhydride is added to the solution, followed by allowing the mixture to stand at room temperature for 3 hours. The reaction solution is poured into ice-cold water, followed by extraction with ethyl acetate. The organic layer is washed with an aqueous sodium hydrogencarbonate solution and water successively, and dried, and the solvent is evaporated off under reduced pressure to give 0.66 g of a colorless oily material of cis-3-acetoxy-4-acetoxymethyl-7-methoxy-4-(2-diethylaminoethyl)-3,4-dihydro-2H-1,5-benzoxathiepin. The hydrochloride salt, when recrystallized from ethanol-ethyl ether, turns into white crystals., m.p. of 177°–179° C.

Elemental analysis, for $C_{21}H_{31}NO_6S.HCl.1/5H_2O$:
Calcd.: C, 54.19; H, 7.01; N, 3.06; Found: C, 54.27; H, 7.05; N, 3.06.

EXAMPLE 28

By the same procedure as described in Example 27, the compound as obtained in Example 12 is acetylated to give methyl cis-3-acetoxy-7-methoxy-4-[3-(4-phenylpiperazin-1-yl)propyl]-3,4-dihydro-2H-1,5-benzoxathiepin-4-carboxylate, which, when recrystallized from ethyl acetate-n-hexane, turns into colorless prisms, m.p. of 168°–170° C. The structure of this product can be determined by an X-ray analysis of crystals.

Elemental analysis, for $C_{27}H_{35}N_2O_6S$: Calcd.: C, 63.01; H, 6.66; N, 5.44; Found: C, 63.01; H, 6.69; N, 5.40.

EXAMPLE 29

By the same procedure as described in Example 24, the compound as obtained in Example 12 is reduced with lithium aluminum hydride to give cis-4-hydroxymethyl-7-methoxy-4-[3-(4-phenylpiperazin-1-yl)propyl]-3,4-dihydro-2H-1,5-benzoxathiepin-3-ol. Recrystallization from ethyl acetate yields colorless needles, m.p. of 163°–165° C.

Elemental analysis, for $C_{24}H_{32}N_2O_4S$: Calcd.: C, 64.84; H, 7.25; N, 6.30; Found: C, 64.76; H, 7.31; N, 6.39.

EXAMPLE 30

In 5 ml of methanol is dissolved 160 mg of methyl cis-3-hydroxy-7-methoxy-4-[3-(4-phenylpiperazin-1-yl)propyl]-3,4-dihydro-2H-1,5-benzoxathiepin-4-carboxylate as obtained in Example 12, and 3 ml of 1N sodium hydroxide is added to the solution, followed by stirring at 60° C. for 1 hour. The reaction solution is concentrated under reduced pressure, and 5 ml of water is added to the residue. The mixture is adjusted to pH 3 to 4 with 1N hydrochloric acid and cooled, and the precipitate is collected by filtration, washed with acetone and dried to give 0.13 g of white crystals of cis-3-hydroxy-7-methoxy-4-[3-(4-phenylpiperazin-1-yl)propyl]-3,4-dihydro-2H-1,5-benzoxathiepin-4-carboxylic acid, m.p. of 250°–260° C. (decomp.).

Elemental analysis, for $C_{24}H_{30}N_2O_5S.H_2O$: Calcd.: C, 60.48; H, 6.77; N, 5.88; Found: C, 60.27; H, 6.73; N, 5.66.

EXAMPLE 31

In 5 ml of N,N-dimethylformamide is dissolved 0.3 g of methyl cis-3-hydroxy-7-methoxy-4-[3-(4-phenylpiperazin-1-yl)propyl]-3,4-dihydro-2H-1,5-benzoxathiepin-4-carboxylate, and 0.08 g of phenyl isocyanate and 0.1 ml of triethylamine are added to the solution, followed by stirring at room temperature for 3 hours. The reaction solution is poured into water, followed by extraction with ethyl acetate. The organic layer is washed with water, dried and concentrated under reduced pressure, and the residue is chromatographed on a column of silica gel. The fractions which are eluted with a mixture of n-hexane: ethyl acetate=3:1 to 1:1 are collected and concentrated under reduced pressure to give 0.4 g of a colorless oily material of methyl cis-7-methoxy-3-phenylcarbamoyloxy-4-[3-(4-phenylpiperazin-1-yl)propyl]-3,4-dihydro-2H-1,5-benzoxathiepin-4-carboxylate. Addition of hydrochloric acid-ethanol solution yields 0.3 g of the hydrochloride salt in the form of a powder.

Elemental analysis, for $C_{32}H_{37}N_3O_6S \cdot 2HCl \cdot \frac{1}{2}H_2O$: Calcd.: C, 57.05; H, 5.99; N, 6.23; Found: C, 56.78; H, 5.96; N, 6.37.

EXAMPLE 32

By the same procedure as described in Example 1, methyl 3-oxo-3,4-dihydro-2H-1,5-benzoxathiepin-4-carboxylate as obtained in Reference Example 24 is allowed to undergo condensation with 3-(4-phenylpiperazin-1-yl)propyl chloride, and methyl 3-oxo-[3-(4-phenylpiperazin-1-yl)propyl]-3,4-dihydro-2H-1,5-benzoxathiepin-4-carboxylate is isolated as the hydrochloride salt. Recrystallization from methanol produces white crystals, m.p. of 176°–178° C.

Elemental analysis, for $C_{24}H_{28}N_2O_4S \cdot HCl \cdot \frac{1}{2}H_2O$ Calcd.: C, 59.67; H, 6.26; N, 5.80; Found: C, 59.49; H, 6.33; N, 5.79.

EXAMPLE 33

By the same procedure as described in Example 12, methyl 3-oxo-[3-(4-phenylpiperazin-1-yl)propyl]-3,4-dihydro-2H-1,5-benzoxathiepin-4-carboxylate hydrochloride is reduced with sodium borohydride, and separation and purification is effected by silica-gel column chromatography (eluent: hexane-ethyl acetate-methanol=10:10:1). The trans and cis derivatives are obtained from the first and second eluates, respectively.

Methyl cis-3-hydroxy-4-[3-(4-phenylpiperazin-1-yl)propyl]-3,4-dihydro-2H-1,5-benzoxathiepin-4-carboxylate dihydrochloride. Recrystallization from methanol-ethyl acetate yields colorless plates, m.p. of 196°–198° C.

Elemental analysis, for $C_{24}H_{30}N_2O_4S \cdot 2HCl$: Calcd.: C, 55.92; H, 6.26; N, 5.43; Found: C, 55.73; H, 6.15; N, 5.51.

Methyl trans-3-hydroxy-4-[3-(4-phenylpiperazin-1-yl)propyl]-3,4-dihydro-2H-1,5-benzoxathiepin-4-carboxylate dihydrochloride.

White powder (amorphous powder).

Elemental analysis, for $C_{24}H_{30}N_2O_4S \cdot 2HCl \cdot 1/3H_2O$: Calcd.: C, 55.28; H, 6.31; N, 5.37; Found: C, 55.29; H, 6.49; N, 5.11.

EXAMPLE 34

In 3 ml of ethanol is dissolved 0.12 g of cis-3-hydroxy-7-methoxy-4-[3-(4-phenylpiperazin-1-yl)propyl]-3,4-dihydro-2H-1,5-benzoxathiepin-4-carboxylic acid as obtained in Example 30, and 50 mg of diethyl sulfate and 100 mg of sodium hydrogencarbonate are added to the solution, followed by heating under reflux for 3 hours. The reaction solution is poured in water, followed by extraction with ethyl acetate. The organic layer is washed with water and dried, and the solvent is evaporated off under reduced pressure. The resulting residue is purified by column chromatography on silica gel (eluent: hexane-ethyl acetate=1:1) to give 50 mg of a colorless oily material of ethyl cis-3-hydroxy-7-methoxy-4-[3-(4-phenylpiperazin-1-yl)propyl]-3,4-dihydro-2H-1,5-benzoxathiepin-4-carboxylate, which turns into a white powder (amorphous powder) as the hydrochloride salt.

Elemental analysis, for $C_{26}H_{34}N_2O_5S \cdot 2HCl \cdot \frac{1}{4}H_2O$: Calcd.: C, 55.36; H, 6.52; N, 4.97; Found: C, 55.30; H, 6.64; N, 4.94.

EXAMPLES 35 TO 36

By the same procedure as described in Example 4, the compounds as shown in Table 5 are obtained from the compounds as obtained in Reference Example 12.

TABLE 5

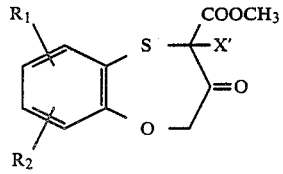

| Ex. No. | $R_1$, $R_2$ | X' | Melting point °C. | Elemental analysis for hydrochloride (parenthesized figures are calculated values) C | H | N | Mass spectrum m/e |
|---|---|---|---|---|---|---|---|
| 35 | 7-$CH_3O$ | $+CH_2)_3N$⟨piperazine⟩N—⟨C₆H₄⟩OCH₃ | Free base 133–135 | $C_{26}H_{32}N_2O_6S \cdot \frac{1}{2}H_2O$ 60.95 (61.27) | 6.30 (6.53) | 5.48 (5.50) | 500(M+) |
| 36 | 7-$CH_3O$ | $+CH_2)_3N$⟨piperazine⟩NCH$_2$—⟨C₆H₅⟩ | Oily material | | | | 484(M+) |

EXAMPLES 37 TO 38

By the same procedure as described in Example 12, the compounds of Examples 35 and 36 are reduced to give the compounds as shown in Table 6.

TABLE 6

[Structure: benzene ring with R₁, R₂ substituents, fused via S and O to a carbon bearing COOCH₃, X', and OH]

| Ex. No. | R₁, R₂ | X' | Configuration | Hydrochloride Melting point, °C. | Elemental analysis for hydrochloride (parenthesized figures are calculated values) C | H | N |
|---|---|---|---|---|---|---|---|
| 37a | 7-CH₃O | $-(CH_2)_3-N\diagup\diagdown N-\bigcirc-OCH_3$ | cis | Powder | C₂₆H₃₄N₂O₆S.2HCl 54.56 (54.26) | 6.29 (6.30) | 5.05 (4.87) |
| 37b | 7-CH₃O | $-(CH_2)_3-N\diagup\diagdown N-\bigcirc-OCH_3$ | trans | Powder | C₂₆H₃₄N₂O₆S.2HCl.½H₂O 53.67 (53.42) | 6.34 (6.38) | 4.68 (4.79) |
| 38a | 7-CH₃O | $-(CH_2)_3-N\diagup\diagdown N-CH_2-\bigcirc$ | cis | Powder | C₂₆H₃₄N₂O₅S.2HCl.H₂O 54.07 (54.07) | 6.61 (6.63) | 4.76 (4.85) |
| 38b | 7-CH₃O | $-(CH_2)_3-N\diagup\diagdown NCH_2-\bigcirc$ | trans | Powder | C₂₆H₃₄N₂O₅S.2HCl.¾H₂O 54.40 (54.49) | 6.41 (6.60) | 4.84 (4.89) |

EXAMPLE 39

A 14 g quantity of methyl cis-4-(3-chloropropyl)-3-hydroxy-7-methoxy-3,4-dihydro-2H-1,5-benzoxathiepin-4-carboxylate as obtained in Reference Example 26, together with 9.0 g of 4-phenylpiperazine, 9.0 g of anhydrous potassium carbonate, 0.5 g of potassium iodide and 100 ml of acetonitrile, is heated under reflux for 20 hours. After the mixture is cooled, the inorganic substance is filtered off, and the filtrate is concentrated under reduced pressure. The residue is dissolved in ethyl acetate, and the organic layer is washed with water and dried. After the solvent is evaporated off under reduced pressure, the residue is purified by column chromatography on silica gel (eluent: hexane:ethyl acetate:methanol=10:10:1), and the resulting oily material is crystallized as the hydrochloride salt to give colorless crystals of methyl cis-3-hydroxy-7-methoxy-4-[3-(4-phenylpiperazin-1-yl)propyl]-3,4-dihydro-2H-1,5-benzoxathiepin-4-carboxylate dihydrochloride, which is identical with the compound as obtained in Example 12. Yield of 8 g.

The product is recrystallized from 50% ethanol to give colorless prisms of methyl cis-3-hydroxy-7-methoxy-4-[3-(4-phenylpiperazin-1-yl)propyl]-3,4-dihydro-2H-1,5-benzoxathiepin-4-carboxylate.monohydrochloride.

m.p. 154°–155° C. (determined on a micro melting point apparatus (Yanagimoto)).

132° C. (decomp.) (determined by the method described in The Pharmacopoeia of Japan).

Elemental analysis, for C₂₅H₃₂N₂O₅S.HCl.2H₂O: Calcd.: C, 55.09; H, 6.84; N, 5.14; Found: C, 55.46; H, 6.77; N, 5.09.

IR $\nu_{max}^{KBr}$ cm⁻¹: 3600–3300, 1735, 1720, 1600, 1480, 1250.

NMR (d₆-DMSO) δ: 1.3–1.8 ppm (2H), 2.7–3.8 ppm (12H), 3.68 ppm (3H, singlet), 3.75 ppm (3H, singlet), 3.8–4.3 ppm (3H), 6.7–7.4 ppm (8H).

EXAMPLES 40 TO 48

By the same procedure as described in Example 39, the compounds as shown in Table 7 are obtained by the substitution reaction of methyl cis-4-(3-chloropropyl)-3-hydroxy-7-methoxy-3,4-dihydro-2H-1,5-benzoxathiepin-4-carboxylate with various amines.

TABLE 7

[Structure: methoxyphenyl fused with S and O to a ring bearing CO₂CH₃, OH, and a propyl chain terminating in X″]

| Ex. No. | X″ | Hydrochloride Melting point, °C. | Elemental analysis for hydrochloride (parenthesized figures are calculated values) C / H / N |
|---|---|---|---|
| 40 | —N(piperidinyl)-C₆H₅ | Powder | $C_{26}H_{33}NO_5S \cdot HCl \cdot \frac{1}{2}H_2O$  60.14  6.69  2.67  (60.39) (6.82) (2.71) |
| 41 | —N(CH₃)CH₂CH₂-(2,3-dimethoxyphenyl) | Powder | $C_{26}H_{35}NO_7S \cdot HCl \cdot \frac{1}{2}H_2O$  56.68  6.97  2.51  (56.67) (6.77) (2.54) |
| 42 | —N(piperidinyl)-C(=O)-C₆H₄-F | Powder | $C_{27}H_{32}FNO_6S \cdot HCl \cdot \frac{1}{2}H_2O$  57.38  5.80  2.40  (57.59) (5.73) (2.49) |
| 43 | —N(piperazinyl)-N-(2-methylphenyl) | Powder | $C_{26}H_{34}N_2O_5S \cdot 2HCl$  55.95  6.52  4.82  (55.81) (6.48) (5.01) |
| 44 | —N(piperazinyl)-N-(4-fluorophenyl) | 140–150 | $C_{25}H_{31}N_2O_5SF \cdot 2HCl \cdot \frac{1}{2}H_2O$  52.71  5.82  4.79  (52.44) (5.99) (4.89) |
| 45 | —N(morpholinyl) | 205–210 | $C_{19}H_{27}NO_6S \cdot HCl$  52.57  6.72  3.19  (52.59) (6.50) (3.23) |
| 46 | —N(piperazinyl)NCH₃ | (Free base 142–145) | $C_{20}H_{30}N_2O_5S \cdot \frac{1}{2}H_2O$  57.45  7.40  6.71  (57.25) (7.45) (6.68) |
| 47 | —N(C₂H₅)₂ | 185–188 | $C_{19}H_{29}NO_5S \cdot HCl$  54.07  7.23  3.34  (54.34) (7.20) (3.34) |
| 48 | —NH-cyclopentyl | Powder | $C_{20}H_{29}NO_5S \cdot HCl \cdot \frac{1}{2}H_2O$  54.51  7.22  3.23  (54.47) (7.09) (3.18) |

EXAMPLE 49

Methyl 7-methyl-3-oxo-3,4-dihydro-2H-1,5-benzoxathiepin-4-carboxylate (1.7 g) is alkylated with 3-(4-phenylpiperazin-1-yl)propylchloride in the same manner as described in Example 1 to give methyl 7-methyl-3-oxo-4-[3-(4-phenylpiperazin-1-yl)propyl]-3,4-dihydro-2H-1,5-benzoxathiepin-4-carboxylate (0.9 g) as a colorless oil.

Mass spectrum (m/e): 454(M+).

IR $\nu_{max}^{neat}$ cm$^{-1}$: 1760, 1730 (C=O).

NMR (CDCl₃) δ: 2.22 ppm(3H, s, C₇—CH₃), 3.72 ppm(3H, s, CO₂CH₃), 4.62 ppm(2H, double doublet, C₂—H).

The hydrochloride [white crystals; mp, 140°–150° C. (decomp.)].

Elemental Analysis for $C_{25}H_{30}N_2O_4S \cdot 2HCl \cdot \frac{1}{2}H_2O$: Calcd.: C, 55.96; H, 6.20; N, 5.22; Found: C, 56.11; H, 6.19; N, 5.11.

EXAMPLE 50

Methyl 7-chloro-3-oxo-3,4-dihydro-2H-1,5-benzoxathiepin-4-carboxylate is alkylated with 3-(4-phenylpiperazin-1-yl)propylchloride in the same manner as described in Example 1 to give methyl 7-chloro-3-oxo-4-[3-(4-phenylpiperazin-1-yl)propyl]-3,4-dihydro-2H-1,5-benzoxathiepin-4-carboxylate which is isolated as the hydrochloride [(white crystals), mp, 197°-199° C.].

Elemental Analysis for $C_{24}H_{27}N_2O_4SCl.2HCl.\frac{1}{4}H_2O$: Calcd.: C, 52.18; H, 5.38; N, 5.07; Found: C, 52.11; H, 5.11; N, 4.98.

EXAMPLE 51

Methyl 7-methyl-3-oxo-4-[3-(4-phenylpiperazin-1-yl)propyl]-3,4-dihydro-2H-1,5-benzoxathiepin-4-carboxylate (0.9 g) is reduced by sodium borohydride in the same manner as described in Example 12 to give methyl cis- and trans-3-hydroxy-7-methyl-4-[3-(4-phenylpiperazin-1-yl)propyl]-3,4-dihydro-2H-1,5-benzoxathiepin-4-carboxylate.

cis-Isomer (colorless oil)

IR $\nu_{max}^{neat}$ cm$^{-1}$: 3450(OH), 1740(C=O)

NMR (CDCl$_3$) δ: 2.35 ppm(3H, s, C$_7$—CH$_3$) 3.75 ppm(3H, s, CO$_2$CH$_3$)

The hydrochloride of cis-isomer (white powder).

Elemental Analysis for $C_{25}H_{32}N_2O_4S.1.5HCl$: Calcd.: C, 58.73; H, 6.60; N, 5.48; Found: C, 58.68; H, 6.96; N, 5.31.

trans-Isomer (colorless oil)

IR $\nu_{max}^{neat}$ cm$^{-1}$: 3550(OH), 1730(C=O)

NMR (CDCl$_3$) δ: 2.25 ppm (3H, s, C$_7$—CH$_3$), 3.52 ppm (3H, s, CO$_2$CH$_3$).

The hydrochloride of trans-isomer (white crystals, mp 145°-155° C.).

Elemental Analysis for $C_{25}H_{32}N_2O_4S.2HCl.\frac{1}{4}H_2O$: Calcd.: C, 56.23; H, 6.51; N, 5.25; Found: C, 56.39; H, 6.53; N, 5.24.

EXAMPLE 52

Methyl 7-chloro-3-oxo-4-[3-(4-phenylpiperazin-1-yl)propyl]-3,4-dihydro-2H-1,5-benzoxathiepin-4-carboxylate is reduced by sodium borohydride in the same manner as described in Example 12 to give methyl cis- and trans-7-chloro-3-hydroxy-4-[3-(4-phenylpiperazin-1-yl)propyl]-3,4-dihydro-2H-1,5-benzoxathiepin-4-carboxylate.

The hydrochloride of cis-isomer (white crystals, mp 205°-207° C.)

Elemental Analysis for $C_{24}H_{29}N_2O_4SCl.2HCl.\frac{1}{2}H_2O$: Calcd.: C, 51.57; H, 5.77; N, 5.01; Found: C, 51.77; H, 5.79; N, 4.97

The hydrochloride of trans-isomer [white crystals, mp 150°-160° C. (decomp.)].

Elemental Analysis for $C_{24}H_{29}N_2O_4SCl.2HCl$: Calcd.: C, 52.42; H, 5.68; N, 5.09; Found: C, 52.24; H, 5.76; N, 4.97.

EXAMPLE 53

Methyl cis-4-(3-chloropropyl)-3-hydroxy-7-methyl-3,4-dihydro-2H-1,5-benzoxathiepin-4-carboxylate 0.3 g is treated with 4-phenylpiperidine in the same manner as described in Example 39 to give methyl cis-3-hydroxy-7-methyl-4-[3-(4-phenylpiperidin-1-yl)propyl]-3,4-dihydro-2H-1,5-benzoxathiepin-4-carboxylate 0.3 g as a colorless oil.

IR $\nu_{max}^{neat}$ cm$^{-1}$: 3530(OH), 1740(C=O)

NMR (CDCl$_3$) δ: 2.22 ppm(3H, s, C$_7$—CH$_3$) 3.72 ppm(3H, s, CO$_2$CH$_3$)

The hydrochloride (white powder).

Elemental Analysis for $C_{26}H_{33}NO_4S.HCl.\frac{1}{2}H_2O$: Calcd.: C, 62.32; H, 7.04; N, 2.80; Found: C, 62.41; H, 7.06; N, 2.70.

EXAMPLE 54

Methyl cis-4-(3-chloropropyl)-3-hydroxy-7-methyl-3,4-dihydro-2H-1,5-benzoxathiepin-4-carboxylate is treated with N-methyl-3,4-dimethoxyphenethylamine in the same manner as described in Example 39 to give methyl cis-3-hydroxy-7-methyl-4-{3-[N-methyl-2-(3,4-dimethoxyphenyl)ethylamino]propyl}-3,4-dihydro-2H-1,5-benzoxathiepin-4-carboxylate which is isolated as the hydrochloride (amorphous powder).

Elemental Analysis for $C_{26}H_{34}NO_6S$ $HCl.\frac{1}{2}H_2O$: Calcd.: C, 58.36; H, 6.97; N, 2.62; Found: C, 58.21; H, 7.21; N, 2.49.

EXAMPLE 55

A mixture of 4-(3-chloropropyl)-7-methoxy-3,4-dihydro-2H-1,5-benzoxathiepin-3-ol 500 mg, N-phenylpiperazine (500 mg), potassium iodide (50 mg), potassium carbonate (400 mg) and N,N-dimethylformamide (10 ml) is heated at 80° C. for 8 hours with stirring. The reaction mixture is poured into water, extracted with ethyl acetate. The organic layer is washed with water, dried over anhydrous sodium sulfate and evaporated to dryness in vacuo. The residue is submited to column chromatography on silica gel eluting with hexane-ethyl acetate-methanol (10:10:1) to give cis-7-methoxy-4-[3-(4-phenylpiperazin-1-yl)propyl]-3,4-dihydro-2H-1,5-benzoxathiepin-3-ol (colorless oil) which is isolated as the dihydrochloride (amorphous powder).

Elemental Analysis for $C_{23}H_{30}N_2O_3S.2HCl.\frac{1}{2}H_2O$: Calcd.: C, 55.64; H, 6.70; N, 5.64; Found: C, 55.95; H, 6.53; N, 5.47.

400 MHz NMR (d$_6$-DMSO) δ: 3.206 ppm(1H, multiplet, J=8.1, 3.8, and 4.6 Hz, C$_4$—H), 3.776 ppm(1H, double doublet, J=12.2 and 8.5 Hz, C$_2$—H), 4.017 ppm(1H, double doublet, J=12.2 and 3.8 Hz, C$_2$—H), 4.152 ppm(1H, double triplet, J=8.5, 3.8 and 3.8 Hz, C$_3$—H).

EXAMPLE 56

To a solution of 7-methoxy-3-oxo-3,4-dihydro-2H-1,5-benzoxathiepin-4-diethylcarboxamide (1.8 g) in ethanol (15 ml) is added sodium borohydride (0.3 g). The reaction mixture is stirred at room temperature for 5 hours, then poured into ice-water and extracted with ethyl acetate. The organic layer is washed with saturated aqueous sodium chloride solution, dried over anhydrous sodium sulfate and evaporated to dryness in vacuo. The obtained residue is submited to column chromatography on silica gel eluting with ethyl acetate-hexane (1:1) to give 3-hydroxy-7-methoxy-3,4-dihydro-2H-1,5-benzoxathiepin-4-diethylcarboxamide (1.48 g) as a colorless oil. (IR$\nu_{max}^{neat}$ cm$^{-1}$: 3400, 1635).

Thus obtained alcohol 300 mg is reduced by sodium monoacetoxyborohydride in the same manner similar to that described in Example 23 and submited to column chromatography on silica gel eluting with methylene chloride-methanol (10:1) to give cis-4-diethylaminomethyl-7-methoxy-3,4-dihydro-2H-1,5-benzoxathiepin-3-ol as a colorless oil which is crystallized as the hydrochloride from methanol-ethyl acetate (pale yellow prisms (138 mg), mp 160°-162° C.).

Elemental Analysis for $C_{15}H_{23}NO_3S\cdot HCl$: Calcd.: C, 53.96; H, 7.25; N, 4.20; Found: C, 54.11; H, 7.44; N, 4.13.

400 MHz NMR (d$_6$-DMSO): 3.719 ppm(1H, double doublet, J=12.5 and 8.31 Hz, C$_2$—H), 3.819 ppm(1H, double triplet, J=7.8, 3.9 and 3.9 Hz, C$_4$—H), 4.121 ppm(1H, double doublet, J=12.5 and 3.9 Hz, C$_2$—H), 4.297 ppm(1H, double triplet, J=8.3, 3.9 and 3.9 Hz, C$_3$—H).

EXAMPLE 57

Methyl cis-7-chloro-4-(3-chloropropyl)-3-hydroxy-3,4-dihydro-2H-1,5-benzoxathiepin-4-carboxylate 0.15 g is treated with N-methyl-2-(3,4-dimethoxyphenyl)ethylamine in the same manner as described in Example 39 to give 0.06 g of methyl cis-7-chloro-3-hydroxy-4-{3-[N-methyl-2-(3,4-dimethoxyphenyl)ethylamino]-propyl}-3,4-dihydro-2H-1,5-benzoxathiepin-4-carboxylate 0.06 g as a colorless oil, which is treated with hydrogen chloride to give the hydrochloride as an amorphous powder.

Elemental Analysis for $C_{25}H_{32}ClNO_6S\cdot HCl\cdot \frac{1}{2}H_2O$: Calcd.: C, 54.05; H, 6.17; N, 2.52; Found: C, 54.05; H, 6.04; N, 2.57.

EXAMPLE 58

Optical resolution of (±) methyl cis-3-hydroxy-7-methoxy-4-[3-(4-phenylpiperazin-1-yl)propyl]-3,4-dihydro-2H-1,5-benzoxathiepin-4-carboxylate (±) Methyl cis-3-hydroxy-7-methoxy-4-[3-(4-2H-1,5-benzoxathiepin-4-carboxylate (1.3 g) and S-(+)-1,1'-binaphthyl-2,2'-diyl hydrogenphosphate (1.0 g) are dissolved in methanol (50 ml). The solution is evaporated in vacuo. The residue is dissolved in acetone-methanol and allowed to stand in a refrigerator. The crystalline deposite is filtered off and recrystallized three times from acetone-methanol to yield white crystals ($[\alpha]_D^{25} + 175.5$ (c=1.01, methanol).

A suspension of the obtained crystals in methylene chloride is treated with 1N sodium hydroxide solution. The organic layer is washed with water, dried over anhydrous sodium sulfate and evaporated in vacuo to give a free base as a colorless oil. The obtained base is dissolved in ethanol, treated with hydrogen chloride and evaporated in vacuo. The residue is triturated with methanol-ethyl ether to give (−) methyl cis-3-hydroxy-7-methoxy-4-[3-(4-phenylpiperazin-1-yl)propyl]-3,4-dihydro-2H-1,5-benzoxathiepin-4-carboxylate dihydrochloride as an amorphous powder.

$[\alpha]_D - 102.0°$ (c=0.54 in methanol)

Elemental Analysis for $C_{25}H_{32}N_2O_5S\cdot 2HCl\cdot \frac{1}{2}H_2O$: Calcd.: C, 54.15; H, 6.36; N, 5.05; Found: C, 53.98; H, 6.18; N, 4.83.

EXAMPLE 59

In the same manner as described in Example 58, the salt of (±) methyl cis-3-hydroxy-7-methoxy-4-[3-(4-phenylpiperazin-1-yl)propyl]-3,4-dihydro-2H-1,5-benzoxathiepin-4-carboxylate and R-(−)-1,1'-binaphthyl-2,2'-diyl hydrogenphosphate is recrystallized three times from acetone-methanol to give white crystals ($[\alpha]_D^{25} - 172°$ (c=1.03, methanol)]. The obtained salt is treated with 1N sodium hydroxide, followed by treatment with hydrogen chloride to give (+) methyl cis-3-hydroxy-7-methoxy-4-[3-(4-phenylpiperazin-1-yl)propyl]-3,4-dihydro-2H-1,5-benzoxathiepin-4-carboxylate dihydrochloride as an amorphous powder.

$[\alpha]_D + 110.8°$ (c=0.48 in methanol)

Elemental Analysis for $C_{25}H_{32}N_2O_5S\cdot 2HCl\cdot \frac{1}{2}H_2O$: Calcd.: C, 54.15; H, 6.36; N, 5.05; Found: C, 54.11; H, 5.93; N, 4.80.

EXAMPLE 60

A mixture of cis-3-acetoxy-4-(3-chloropropyl)-7-methoxy-3,4-dihydro-2H-1,5-benzoxathiepin-4-N-benzylcarboxamide (0.3 g), N-phenylpiperazine (0.13 g), potassium iodide (0.1 g), potassium carbonate (0.12 g) and N,N-dimethylformamide (4 ml) is stirred at 70° C. for 2 hours. The reaction mixture is poured into ice-water (20 ml) and extracted with ethyl acetate. The organic layer is washed with water, dried over anhydrous $Na_2SO_4$ and evaporated to dryness in vacuo. The residue is triturated with AcOEt-hexane to give cis-3-acetoxy-7-methoxy-4-[3-(4-phenylpiperazine-1-yl)propyl]-3,4-dihydro-2H-1,5-benzoxathiepin-4-N-benzylcarboxamide (97 mg) which is isolated as white crystals, mp 178°–180° C. (from AcOEt)

Mass Spectrum m/e: 589 (M+)

Elemental Analysis for $C_{33}H_{39}N_3O_5S\cdot \frac{1}{4}H_2O$: Calcd.: C, 66.70; H, 6.70; N, 7.07; Found: C, 66.75; H, 6.63; N, 6.87.

EXAMPLE 61

Methyl cis-4-(3-chloropropyl)-3-hydroxy-7-methoxy-3,4-dihydro-2H-1,5-benzoxathiepin-4-carboxylate is treated with 4-(2-pyrimidyl)piperazine in the same manner as described in Example 39 to give methyl cis-3-hydroxy-7-methoxy-4-[3-[4-(2-pyrimidyl)piperazin-1-yl]propyl]-3,4-dihydro-2H-1,5-benzoxathiepin-4-carboxylate dihydrochloride as an amorphous powder.

Elemental Analysis for $C_{23}H_{30}N_4O_5S\cdot 2HCl\cdot 3/2H_2O$: Calcd.: C, 48.08; H, 6.14; N, 9.75; Found: C, 47.93; H, 6.25; N, 9.56.

EXAMPLE 62

Methyl cis-3-hydroxy-4-(3-chloropropyl)-8-methoxy-3,4-dihydro-2H-1,5-benzoxathiepin-4-carboxylate is treated in the same manner as described in Example 39 to give methyl cis-3-hydroxy-8-methoxy-4-[3-(4-phenylpiperazin-1-yl)propyl]-3,4-dihydro-2H-1,5-benzoxathiepin-4-carboxylate hydrochloride as colorless crystals.

Melting point: 195°–198° C. (recrystallized from ethanol)

Elemental Analysis for $C_{25}H_{32}N_2O_5S\cdot HCl\cdot \frac{1}{4}H_2O$: Calcd.: C, 58.47; H, 6.57; N, 5.46; Found: C, 58.43; H, 6.44; N, 5.62.

EXAMPLE 63

Methyl trans-3-hydroxy-8-methoxy-4-(3-chloropropyl)-3,4-dihydro-2H,-1,5-benzoxathiepin-4-carboxylate is treated in the same manner as described in Example 39 to give methyl trans-3-hydroxy-8-methoxy-4-[3-(4-phenylpiperazin-1-yl)propyl]-3,4-dihydro-2H-1,5-benzoxathiepin-4-carboxylate dihydrochloride as colorless crystals.

Melting point: 160°–175° C. (decomp.) (recrystallized from ethanol-ethyl ether)

Elemental Analysis for $C_{25}H_{32}N_2O_5S\cdot 2HCl\cdot \frac{1}{2}H_2O$: Calcd.: C, 54.12; H, 6.36; N, 5.05; Found: C, 54.08; H, 6.02; N, 5.03.

EXAMPLE 64

A mixture of methyl cis-7-benzyloxy-3-hydroxy-4-[3-(4-phenylpiperazin-1-yl)propyl]-3,4-dihydro-2H-1,5-benzoxathiepin-4-carboxylate dihydrochloride (0.8 g), methanol (100 ml), concentrated hydrochloric acid (0.3 ml) and 10% palladium carbon (1.8 g) is hydrogenated under hydrogen stream at room temperature for 48 hours. After filtration, the filtrate is evaporated to dryness in vacuo.

The residue is mixed with ethyl acetate and 5% sodium bicarbonate solution. The organic layer is separated, washed with water, dried over anhydrous sodium sulfate and evaporated to dryness in vacuo. The residue is submitted to silica gel column chromatography eluting with n-hexane-ethyl acetate (2:3) to give methyl cis-3,7-dihydroxy-4-[3-(4-phenylpiperazin-1-yl)propyl]-3,4-dihydro-2H-1,5-benzoxathiepin-4-carboxylate as white crystals.

Melting point: 195°–197° C. (recrystallized from ethyl acetate)

Elemental Analysis for $C_{24}H_{30}H_2O_5S$: Calcd.: C, 62.86; H, 6.59; N, 6.11; Found: C, 62.61; H, 6.50; N, 5.88.

EXAMPLE 65

A mixture of methyl cis-4-(3-chloropropyl)-3-hydroxy-7-methoxy-3,4-dihydro-2H-1,5-benzoxathiepin-4-carboxylate (2.0 g), 1N NaOH (8 ml) and methanol (20 ml) is stirred at room temperature for 14 hours. The reaction mixture is poured into water and washed with ethyl acetate. The aqueous layer is acidified with 6N HCl and extracted with ethyl acetate. The organic layer is washed with water, dried over anhdrous sodium sulfate and evaporated to dryness in vacuo. The residue is recrystallized from ethyl acetate to give cis-4-(3-chloropropyl)-3-hydroxy-7-methoxy-3,4-dihydro-2H-1,5-benzoxathiepin-4-carboxylic acid as colorless prisms (mp: 174°–176° C.). The obtained acid (0.7 g) is heated at 180° C. for 30 minutes to give trans-4-(3-chloropropyl)-7-methoxy-3,4-dihydro-2H-1,5-benzoxathiepin-3-ol as a colourless oil.

A mixture of trans-4-(3-chloropropyl)-7-methoxy-3,4-dihydro-2H-1,5-benzoxathiepin-3-ol (0.1 g) and N-phenylpiperazine (0.2 g) is stirred at 90° C. for 2 hours. The reaction mixture is purified by silica gel column chromatography eluting with n-hexane-ethyl acetate methanol (10:10:1) and treated with ethanolic hydrogen chloride to give trans-7-methoxy 4-[3-(4-thenylpiperazin-1-yl)propyl]-3,4-dihydro-2H-1,5-benzoxathiepin-3-ol dihydrochloride as an amorphous powder.

Elemental Analysis for $C_{23}H_{30}N_2O_3S \cdot 2HCl$: Calcd.: C, 56.67; H, 6.62; N, 5.44; Found: C, 56.42; H, 6.85; N, 5.51.

EXAMPLE 66

A mixture of 1.0 g of methyl cis-4-(3-chloropropyl)-3-hydroxy-7-methoxy-3,4-dihydro-2H-1,5-benzoxathiepin-4-carboxylate, 0.67 g of N-4-hydroxyphenylpiperazine and 2 ml of N,N-dimethylacetamide is stirred at 90° C. for 3 hours. Water is added to the mixture and the mixture is extracted with ethyl acetate. The organic layer are combined, washed with water and dried and the solvent is evaporated off under reduced pressure. The residue is purified by silica gel column chromatography [eluent: hexane-ethyl acetate-methanol (20:20:1)] to give 0.7 g of methyl cis-3-hydroxy-4-[3-[4-(4-hydroxyphenyl)piperazin-1-yl]propyl]-7-methoxy-3,4-dihydro-2H-1,5-benzoxathiepin-4-carboxylate as a pale yellow oil. This product is converted to a white powder of the dihydrochloride.

Melting point: 240°–245° C. (decomp.)

Elemental Analysis for $C_{25}H_{32}N_2O_6S \cdot 2HCl$; Calcd.: C, 53.47; H, 6.10; N, 4.99; Found: C, 53.20; H, 5.97; N, 5.21.

EXAMPLE 67

A mixture of 1.0 g methyl cis-4-(3-chloropropyl)-3-hydroxy-7-methoxy-3,4-dihydro-2H-1,5-benzoxathiepin-4-carboxylate, 1.2 g of N-2-hydroxyphenylpiperazine, 0.97 g of potassium carbonate and 6 ml of N,N-dimethylacetamide is stirred at 85° C. for 5 hours. Water is added to the mixture and the mixture is extracted with ethyl acetate. The organic layers are combined, washed with water and dried and the solvent is evaporated off under reduced pressure. The residue is purified by silica gel column chromatography [eluent: hexane-ethyl acetate-methanol (20:20:1)] to give 0.7 g of methyl cis-3-hydroxy-4-[3-[4-(2-hydroxyphenyl)piperazin-1-yl]propyl]-7-methoxy-3,4-dihydro-2H-1,5-benzoxathiepin-4-carboxylate as a pale yellow oil. This product is converted to a white powder of the dihydrochloride.

Melting point: 175°–190° C. (decomp.)

Elemental Analysis for $C_{25}H_{32}H_2O_6S \cdot 2HCl \cdot \frac{1}{2}H_2O$: Calcd.: C, 52.63; H, 6.18; N, 4.91; Found: C, 52.91; H, 5.94; N, 4.95.

EXAMPLE 68

To 600 ml of methanol is dissolved in 1.16 g of methyl cis-7-benzyloxy-3-hydroxy-4-[3-[4-(4-hydroxyphenyl)piperazin-1-yl]propyl]-3,4-dihydro-2H-1,5-benzoxathiepin-4-carboxylate, and 1.0 g of 10% palladium carbon and 0.1 ml of concentrated hydrochloric acid are added to the mixture, followed by stirring under hydrogen atmosphere at ambient temperature and under atmospheric pressure. The catalyst is filtered off and the solvent is evaporated off. The residue is purified by silica gel column chromatography [eluent: hexane-ethyl acetate-methanol (12:12:1)]. The obtained crude product is recrystallized from ethyl acetate to give 0.62 g of methyl cis-3,7-dihydroxy-4-[3-[4-(4-hydroxyphenyl)piperazin-1-yl]propyl]-3,4-dihydro-2H-1,5-benzoxathiepin-4-carboxylate as a white powder. Melting point: 226°–229° C.

Elemental Analysis for $C_{24}H_{30}N_2O_6S$: Calcd.: C, 60.74; H, 6.37; N, 5.90; Found: C, 60.47; H, 6.39; N, 5.71.

Melting points in Reference Examples and Examples shows the values as measured by a micro melting point apparatus (Yanagimoto, Japan) unless otherwise specified.

EXPERIMENT EXAMPLE 1

Serotonin $S_2$-receptor blocking activity (in vitro) of the compound of the present invention:

[Experimental method]

The experiment was carried out in accordance with the method of Bevan & Osher (Agents Actions, 2, 257, 1972) with a few modifications. The heart removed from a hog immediately after being slaughtered at a slaughterhouse was preserved under ice-cooling, and the left circumflex coronary artery was dissected within 3 hours. The coronary artery was cut into a ring preparation of about 3 mm in width, which was suspended in a double-wall organ bath containing 20 ml of the Krebs-Henseleit solution using a pair of suspending hooks. One of the suspending hooks was fixed to the bottom of the organ bath, while the other was connected to a strain-gaige transducer, and the constriction of the ring preparation of the porcine coronary artery was isometrically measured and recorded on a polygraph recorder. The organ bath was maintained at 37° C., and the Krebs-Henseleit solution was saturated with a mixed gas of 97% $O_2$+3% $CO_2$, with the Krebs-Henseleit solution being composed of 118.3 mM NaCl, 4.7 mM KCl, 1.2 mM $KH_2PO_4$, 2.58 mM $CaCl_2.2H_2O$, 1.15 mM $MgSO_4.7H_2O$, 25 mM $NaHCO_3$ and 11.1 mM glucose.

In 1 to 2 hours when the blood vessel preparation showed stable resting tension, the resting tension was readjusted to be 2 g, and $10^{-6}$M serotonin (final concentration) was added to the organ bath at the interval of about 1 hour to check the responsiveness of the preparation. When the reaction of the blood vessel to 2 to 3 additions of serotonin became stable, a concentration of the test compound was added to the organ bath 10 minutes prior to subsequent addition of serotonin. The serotonergic blocking effect of the test compound was calculated from the magnitudes of constriction caused by serotonin before and after the addition of the test compound.

[Experimental results]

The results of the experiment with regard to the compounds of the present invention are shown in Table 8.

TABLE 8

Serotonin $S_2$-receptor blocking effect in porcine coronary artery preparation.

| Example number | Concn. (M) | No. of cases | Inhibition of constriction by serotonin, % |
|---|---|---|---|
| 1 | $10^{-5}$ | 3 | 85.7 ± 9.7 |
| | $10^{-6}$ | 3 | 67.2 ± 8.0 |
| 12-(cis-isomer. hydrochloride) | $10^{-6}$ | 3 | 100 |
| | $10^{-7}$ | 4 | 76.0 ± 5.3 |
| 28 | $10^{-5}$ | 3 | 93.3 ± 6.9 |
| | $10^{-6}$ | 3 | 73.5 ± 10.2 |
| 34 | $10^{-5}$ | 2 | 100 |
| | $10^{-6}$ | 3 | 83.3 ± 1.0 |
| 41 | $10^{-5}$ | 2 | 82.8 |
| | $10^{-6}$ | 3 | 27.2 ± 1.5 |
| 40 | $10^{-6}$ | 3 | 87.8 ± 3.0 |
| | $10^{-7}$ | 3 | 24.7 ± 2.2 |
| 44 | $10^{-6}$ | 3 | 99.2 ± 0.8 |
| | $10^{-7}$ | 3 | 12.2 ± 37.0 |
| 33 | $10^{-6}$ | 2 | 77.3 |
| (cis-isomer) | $10^{-7}$ | 2 | 2.6 |
| 26 | $10^{-5}$ | 2 | 99.8 |
| | $10^{-6}$ | 2 | 35 |
| 42 | $10^{-6}$ | 3 | 87.5 ± 9.0 |
| | $10^{-7}$ | 3 | 50.4 ± 7.0 |

EXPERIMENT EXAMPLE 2

In the same manner as described in Experiment Example 1, the serotonergic blocking effect of the test compound was measured. The results are shown in Table 9.

TABLE 9

| Example number | Concn. (M) | No. of cases | Inhibition of constriction by serotonin (%) |
|---|---|---|---|
| 39 (monohydrochloride) | $10^{-7}$ | 3 | 57 ± 7.1 |
| 59 | $10^{-7}$ | 3 | 70.7 ± 2.0 |

EXPERIMENT EXAMPLE 3

Oral serotonergic blocking activity of the compounds of the present invention.

[Experimental method]

The experiment was carried out using beagle dogs of male weighing from 10 to 14 kg. Polyethylene tubes were previously implanted into the femoral artery and vein for measurement of systemic blood pressure and intravenous administration of a test compound, respectively. The surgical operation for implantation of the polyethylene tubes was performed under strile conditions under anesthesia with sodium pentobarbital (30 mg/kg intravenously administered). The other ends of the polyethylene tubes were led to the dorsal part subcutaneously and exteriorized.

Two to 3 days after the operation, the experiment was carried out. The polyethylene tube kept inserted into the artery was connected to a pressure transducer, and the systemic blood pressure was measured and recorded continuously on a polygraph recorder. When 3 to 30 μg/kg of serotonin was administered intravenously through the polyethylene tube kept inserted into the femoral vein, a transient hypertensive reaction was observed in a dose-dependent manner, and when 30 μg/kg of serotonin was, for example, given repeatedly at the interval of about 30 minutes, a reproducible hypertensive reaction was noted. Therefore, 30 μg/kg of serotonin was used in order to investigate into the effect through oral administration of the compound of the present invention. After it was confirmed that 2 to 3 intravenous administrations of 30 μg/kg of serotonin at the interval of about 30 minutes gave rise to a stable hypertensive reaction, the compound (I) of the present invention [Example 12 (cis isomer.dihydrochloride)] was administered orally in doses of 0.1, 0.3 and 1.0 mg/kg, and the hypertensive reaction to 30 μg/kg of serotonin was repeatedly examined, thereafter, until the pre-drug level of the hypertension reaction was attained.

[Experiment results]

The results of the experiment are shown in Table 10. The compound of Example 12 (cis isomer.dihydrochloride), when given in doses of not less than 0.1 mg/kg, exhibited dose-dependent and persisting inhibition against the hypertensive reaction to serotonin.

TABLE 10

Inhibition of the hypertensive reaction to serotonin (30 μg/kg, i.v.) in unanesthetized beagle dogs.

| Dose mg/kg | No. of cases | Maximum inhibition % | The time when the maximum inhibition developed hr. after administration | Duration hr. |
|---|---|---|---|---|
| 0.1 | 4 | 27.8 | 2 | 4 |
| 0.3 | 4 | 40.9 | 3 | 6 |
| 1.0 | 3 | 72.0 | 3 | 8 |

EXPERIMENT EXAMPLE 4

Calcium-antagonistic action

[Experimental method]

The mesenterium was excised from a spontaneously hypertensive rat (14 weeks of age, male), and perfused through the mesenteric artery with the Krebs-Henseleit solution under warming at 37° C. The basal flow rate was kept in about 4 ml/min for the perfusion pressure to be about 40 mmHg. Employed as an indication of calcium antagonism was inhibition of the increase in the perfusion pressure provoked by 10 mg/preparation of KCl injected into the mesenteric artery. The test compound was injected into the artery 30 minutes prior to the injection of KCl.

[Experimental results]

The results are shown in Table 11. In the cases of non-treatmented, control group, the increase in the perfusion pressure due to KCl was 73±20 (mean value for 8 cases±S.E.M.) mmHg, which was designated as 100% in the table. The compound of Example 12 (cis), when given in doses of $10^{-7}$ to $3\times10^{-6}$M, exhibited dose-dependent and significant inhibition of the KCl-induced increase in the perfusion

TABLE 11

Calcium antagonistic action in isolated, perfused mesenterial preparations of rats.

| Group | Dose (M) | Change in perfusion pressure upon injection of KCl (%) (No. of cases) |
|---|---|---|
| Control | — | 100 (8) |
| Example 12 (cis) | $10^{-7}$ | 84 ± 3* (3) |
| | $10^{-6}$ | 51 ± 14* (5) |
| | $3 \times 10^{-6}$ | 30 ± 2* (3) |

EXPERIMENT EXAMPLE 5

Diuretic action

[Experimental method]

Four groups of 5 spontaneously hypertensive rats (13 week of age, male) each were used in the experiment. The test compound was suspended in isotonic saline with a small amount of gum arabic and administered orally in the volume of 25 ml/kg. Isotonic saline containing gum arabic alone was given to the control group. After the administration, each rat was placed in a metabolism cage for collection of urine for 5 hours. The volume of urine and the amounts of urinary Na+ and K+ excreted were measured. The concentrations of Na+ and K+ were determined using a flame spectrophotometer (Hitachi type 205 DT).

[Experimental results]

The results are shown in Table 12. The compound of Example 12 (cis isomer.dihydrochloride), when administered orally in a dose of 3 mg/kg, tended to promote the secretion of urine as well as of Na+ and K+, and when given orally in a dose of 10 mg/kg, brought about a significant increase in the urinary volume, and tendency toward increases in Na+ and K+ excretion. Thirty mg/kg gave rise to significant increases in the urinary volume and in Na+ and K+ excretion.

TABLE 12

Diuretic action in spontaneously hypertensive rats.

| Group | Dose mg/kg orally | No. of animals | Volume of urine ml/100 g/5 hr | Na+ μeq/100 | K+ g/5 hr |
|---|---|---|---|---|---|
| Control | — | 5 | 1.02 ± 0.10 | 128 ± 15 | 59 ± 8 |
| Example 12 (cis) | 3 | 5 | 1.41 ± 0.18 | 160 ± 19 | 77 ± 5 |
| | 10 | 5 | 1.74 ± 0.15* | 169 ± 20 | 81 ± 8 |
| | 30 | 5 | 1.97 ± 0.20** | 192 ± 15* | 88 ± 9* |

Student's t-test
*P < 0.05,
**P < 0.01

EXPERIMENT EXAMPLE 6

In vivo antithrombotic action in the coronary circulation of anesthetized dogs.

[Experimental method]

Adult mongrel dogs, which underwent thoracotomy under anesthesia with sodium pentobarbital, were used. Intracoronary thrombosis was produced in accordance with the method of Folts et al. [Circulation, 54, 365 (1976)]. In brief, an arterial cannula was inserted into the left circumflex coronary artery, and the arterial blood was led from the common carotid artery through an extracorporeal circuit to perfuse the arterial area. The coronary blood flow was measured with an electromagnetic blood flow probe placed in the extracorporeal circuit. A plastic constrictor was set around the circumflex coronary artery to narrow it by about 70 to 80%. The formation of intra-coronary thrombi was judged by the periodically found decrease and increase in coronary blood flow, because it was demonstrated that platelet thrombi are formed at the narrowed region due to turbulent blood flow, and washed away by increased pressure gradient. And the frequent formation and removal of the thrombi results in periodical change of the coronary blood flow. Thus, the in vivo anti-thrombotic activity was assessed in terms of the effect of the test compound on the frequency of the change in the coronary blood flow.

The test compound was administered intravenously.

[Experimental results]

When the constrictor was set around the circumflex coronary artery, the coronary blood flow decreased gradually from the initial rate of 20-30 ml/min to several ml/min, and increased abruptly. The decrease and increase in the coronary blood flow were found to take place periodically, and the frequency was 5 to 15/30 minutes.

The compound of Example 12 (cis isomer.dihydrochloride), when administered intravenously in doses of 1 μg/kg and more, was demonstrated to diminish the frequency of the periodical changes in the coronary blood flow in a dose-dependent manner (Table 13), indicating that the compound of Example 12 (cis isomer.dihydrochloride) inhibited the formation of intra-coronary thrombi caused by blood flow disturbances in vivo.

TABLE 13

Effect on the frequency of periodical changes in the coronary blood flow.

| Dose | Before administration | 0 to 30 min. after administration | 30 to 60 min. after administration |
|---|---|---|---|
| 1 μg/kg | 8.86 ± 1.94 | 5.71 ± 1.06 | 3.8 ± 2.62 |
| 3 | 7.25 ± 1.03 | 4.75 ± 1.80 | 0*** |
| 10 | 8.0 ± 1.73 | 0.33 ± 0.33* | 0*** |

The values denote the frequency of periodical changes in the coronary blood flow over the 30-minute period in terms of mean value ± standard error.
*P < 0.05,
***P < 0.001

EXPERIMENTAL EXAMPLE 7

An action to relieve cerebral vasospasm after experimental subarachnoideal hemorrhage

[Experimental method]

Six beagle dogs weighing 10 to 14 kg were used. For cerebrovascular angiography, a polyethylene cannula was previously implanted chronically into the right vertebral artery under pentobarbital anesthesia (30 mg/kg, intravenous administration). Under pentobarbital anesthesia, cerebrovascular angiography was done twice every 2 seconds immediately after injection of 10 ml of a contrast media, iodamide glutamine injection, through the chronically implanted cannula by use of a roentogenograph (MEDIX-50U). Subarachnoideal hemorrhage was induced in injection of 5 ml of fresh autologous blood taken from a vein of the lower extremity into the cisterna magna with a spinal needle under pentobarbital anesthesia 2 days after implantation of the cannula. Cerebrovascular angiography was done before, and 3, 6 and 13 days after subarachnoideal hemorrhage, and the diameter of the basilar artery was measured on the X-ray photograph.

The animals were divided into 2 groups of 3 head each, and the one group was taken as the control, and the other group was given the compound of Example 39 (monohydrochloride salt). The compound concerned was given at doses of 30 mg/kg orally at the day of subarachnoideal hemorrhage, of 1 mg/kg intravenously immediately after subarachnoideal hemorrhage, and of 30 mg/kg orally consecutively every day until the 13th day after subarachnoideal hemorrhage.

[Experimental results]

The diameter of the basilar artery before subarachnoideal hemorrhage and change in the diameter after subarachnoideal hemorrhage are shown in Table 14. In the control group, the basilar arterial diamter decreased by about 40 and 60% 3 and 6 days after subarachnoideal hemorrhage, respectively, indicating occurrence of cerebral vasospasm. On the other hand, in the group treated with the compound, the decrease in the basilar arterial diamter was slight, and the degree of the decrease was significantly lower as compared with that in the control group.

TABLE 14

| Group | Arterial diameter before subarachnoideal hemorrhage (mm) | Change in arterial diameter after subarachnoideal hemorrhage (%) | | |
|---|---|---|---|---|
| | | 3 days after | 6 days after | 13 days after |
| Control group | 1.47 ± 0.02 | −38.3 ± 3.7 | −59.3 ± 3.8 | −12.7 ± 9.9 |
| Treated group | 1.07 ± 0.07* | −2.7 ± 2.7** | −20.7 ± 12.0* | −5 ± 5 |

*$P < 0.05$
**$P < 0.01$
(Student t-test)

EXPERIMENT EXAMPLE 8

An action to improve renal circulation

[Experimental method]

Beagle dogs (normal blood pressure) weighing 9 to 14 kg were used. Laparotomy was done along the abdominal middle line under pentobarbital anesthesia. In order to measure renal blood flow, the left renal artery was dissected free, and an electromagnetic flow probe was set around the artery. A polyethylene tubing was retrogradely inserted and fixed into the abdominal aorta to measure systemic blood pressure. The other ends of the lead wire of the electromagnetic flow probe and of the polyethylene tubing were passed beneath the skin and exteriorized at the back of the neck.

One week or more after the surgical operation, the animals were subjected to the experiment under unanesthetized condition. Renal blood flow was measured by an electromagnetic flowmeter, and systemic blood pressure by a pressure transducer. Heart rate was measured with a pulserate tachometer triggered by blood pressure pulse waves.

The test compound [Example 39 (monohydrochloride salt)] was orally administered, and an interval of 3 days or more was allowed to elapse between administrations, when the compound was administered repeatedly in the same individual.

[Experimental results]

In this series of experiment, when lactose (10 mg/kg, the number of experiments: 7) was orally administered as a control, no change in systemic blood pressure, heart rate and renal blood flow was noted over 7 hours of observation period. By administration of 3 or 10 mg/kg of the test compound, systemic blood pressure was slightly lowered in a dose-dependent manner, while heart rate was not affected. Renal blood flow, however, was markedly increased by these doses, the maximum increases being by about 23 and 46%, respectively, and the action lasted over 7 hours of observation. The results are shown in Table 15.

TABLE 15

| Doses (mg/kg, orally) | No. of experimental cases | Maximum changes 2 to 3 hours after administration (%) | | |
|---|---|---|---|---|
| | | Systemic blood pressure | Heart rate | Renal blood pressure |
| 3 | 3 | −6.6 ± 4.0 | +2.8 ± 3.7 | +23.2 ± 9.4 |
| 10 | 3 | −11.3 ± 0.9 | +3.8 ± 5.9 | +46.1 ± 8.0 |

EXPERIMENT EXAMPLE 9

In the same manner as described in Experiment Example 1, the serotonergic blocking effect of the test compound was measured. The results are shown in Table 16.

TABLE 16

| Example number | Concn. (M) | Inhibition of constriction by serotonin (%) |
|---|---|---|
| 61 | $10^{-5}$ | 68 |
| 62 | $10^{-5}$ | 92 |
| | $10^{-6}$ | 71 |
| 63 | $10^{-5}$ | 96 |
| 64 | $10^{-5}$ | 79 |
| 65 | $10^{-5}$ | 72 |
| 66 | $10^{-5}$ | 100 |
| | $10^{-6}$ | 100 |
| | $10^{-7}$ | 62 |
| 67 | $10^{-5}$ | 100 |
| 68 | $10^{-5}$ | 100 |

PREPARATION EXAMPLE

The compounds (I) of the present invention can be used, for example, as a treatment agent for ischemic cardiopathies, in the following examples of formulation.

1. Tablets.

| | |
|---|---|
| (1) Methyl cis-3-hydroxy-7-methoxy-4-[3-(4-phenyl-piperazin-1-yl)propyl]-3,4-dihydro-2H—1,5-benzoxathiepin-4-carboxylate.hydrochloride | 10 g |
| (2) Lactose | 90 g |
| (3) Corn starch | 29 g |
| (4) Magnesium stearate | 1 g |
| For 1000 tablets, | 130 g |

The above ingredients (1) and (2) and 17 g of (3) are blended, and granulated together with a paste prepared from 7 g of the ingredient (3). 5 g of the ingredient (3) and the ingredient (4) are added to the resulting granules, and the mixture is compressed by a tabletting machine to prepare 1000 tablets of diameter of 7 mm each containing 10 mg of the ingredient (1).

2. Capsules

| | |
|---|---|
| (1) Methyl cis-3-hydroxy-7-methoxy-4-[3-(4-phenyl-piperazin-1-yl)propyl]-3,4-dihydro-2H—1,5-benzoxathiepin-4-carboxylate.hydrochloride | 10 g |
| (2) Lactose | 135 g |
| (3) Finely powdered cellulose | 70 g |
| (4) Magnesium stearate | 5 g |
| For 1000 capsules, | 220 g |

All of the above ingredients are blended and filled into 1000 capsules of Gelatin Capsule No. 3 (X Japanese Pharmacopoeia) to preapre 1000 capsules each containing 10 mg of the ingredient (1).

3. Injectable solution.

| | |
|---|---|
| (1) Methyl cis-3-hydroxy-7-methoxy-4-[3-(4-phenyl-piperazin-1-yl)propyl]-3,4-dihydro-2H—1,5-benzoxathiepin-4-carboxylate.tartarate | 10 g |
| (2) Sodium chloride | 9 g |
| (3) Chlorobutanol | 5 g |

All of the ingredients are dissolved in 1000 ml of distilled water, and charged into 1000 brown ampoules each containing 1 ml of the solution. The air in the ampoules is replaced with nitrogen gas and the ampoules are sealed. The entire preparation steps are conducted under strile conditions.

What is claimed is:

1. A compound of the formula:

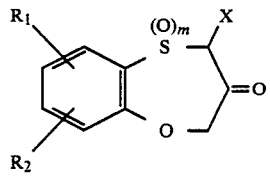

wherein
R$_1$ and R$_2$ are independently hydrogen, halogen, hydroxy, C$_{1-4}$ alkyl or C$_{1-4}$ alkoxy,
X is (1) hydrogen, (2) C$_{1-4}$ alkyl, (3) C$_{1-4}$ alkanoyl, (4) hydroxymethyl, (5) C$_{1-5}$ alkanoyloxymethyl, (6) phenyl-C$_{1-4}$ alkyl which may be substituted by 1 to 3 members of halogen, C$_{1-4}$ alkyl, C$_{1-4}$ alkoxy, methylenedioxy, amino, nitro or hydroxy, (7) phenyl which may be substituted by 1 to 3 members of halogen, C$_{1-4}$ alkyl, C$_{1-4}$ alkoxy, methylenedioxy, amino, nitro or hydroxy, (8) C$_{1-4}$ alkoxycarbonyl, (9) phenyl-C$_{1-4}$ alkoxycarbonyl, (10) carbamoyl which may be substituted by 1 to 2 members of C$_{1-4}$ alkyl, phenyl or phenyl-C$_{1-4}$ alkyl or (11) carboxy, and
m is an integer of 0 to 2, or a salt thereof.

2. A compound according to claim 1, wherein R$_1$ and R$_2$ are independently hydrogen or C$_{1-4}$ alkoxy.

3. A compound according to claim 1, wherein X is hydrogen, carboxy, C$_{1-4}$ alkoxycarbonyl, hydroxymethyl or C$_{1-5}$ alkanoyl-oxymethyl.

4. A compound according to claim 1, wherein X is C$_{1-4}$ alkoxycarbonyl.

5. A compound according to claim 1, wherein m is 0.

6. A compound according to claim 1, wherein R$_1$ is hydrogen and R$_2$ is C$_{1-4}$ alkoxy.

7. A compound according to claim 1, wherein R$_1$ is hydrogen, R$_2$ is C$_{1-4}$ alkoxy which is attached at the 7th position of the benzoxathiepin moiety, X is C$_{1-4}$ alkoxycarbonyl, and m is 0.

8. A compound according to claim 1, which is methyl 7-methoxy-3-oxo-3,4-dihydro-2H-1,5-benzoxathiepin-4-carboxylate.

9. A compound of the formula:

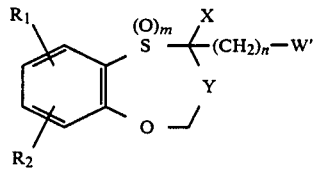

wherein
R$_1$ and R$_2$ are independently hydrogen, halogen, hydroxy, C$_{1-4}$ alkyl or C$_{1-4}$ alkoxy.
X is (1) hydrogen, (2) C$_{1-4}$ alkyl, (3) C$_{1-4}$ alkanoyl, (4) hydroxymethyl, (5) C$_{1-5}$ alkanoyloxymethyl, (6) phenyl-C$_{1-4}$ alkyl which may be substituted by 1 to 3 members of halogen, C$_{1-4}$ alkyl, C$_{1-4}$ alkoxy, methylenedioxy, amino, nitro or hydroxy, (7) phenyl which may be substituted by 1 to 3 members of halogen, C$_{1-4}$ alkyl, C$_{1-4}$ alkoxy, methylenedioxy, amino, nitro or hydroxy, (8) C$_{1-4}$ alkoxycarbonyl, (9) phenyl-C$_{1-4}$ alkoxycarbonyl, (10) carbamoyl which may be substituted by 1 to 2 members of C$_{1-4}$ alkyl, phenyl or phenyl-C$_{1-4}$ alkyl or (11) carboxy,
Y is C=O or CH—OR$_5$
in which R$_5$ is (i) hydrogen, (ii) C$_{1-6}$ alkanoyl, (iii) phenyl C$_{1-6}$ alkanoyl unsubstituted or substituted by 1 to 3 members of halogen, C$_{1-4}$ alkyl, C$_{1-4}$ alkoxy, methylenedioxy, amino, nitro or hydroxy, (iv) carbamoyl unsubstituted or substituted by (1) C$_{1-4}$ alkyl, (2) phenyl unsubstituted or substituted by 1 to 3 members of halogen, C$_{1-4}$ alkyl, C$_{1-4}$ alkoxy, methylenedioxy, amino, nitro or hydroxy or (3) phenyl-C$_{1-4}$ alkyl unsubstituted or substituted by 1 to 3 members of halogen, C$_{1-4}$ alkyl, C$_{1-4}$ alkoxy, methylenedioxy, amino, nitro or hydroxy,
W' is halogen or a group represented by the formula:

$$R'-SO_2-O-$$

wherein
R' is C$_{1-4}$ alkyl, phenyl or p-tolyl,
m is an integer of 0 to 2, and
n is an integer of 1 to 6, or a salt thereof.

10. A compound according to claim 9, wherein $R_1$ and $R_2$ are independently hydrogen or $C_{1-4}$ alkoxy.

11. A compound according to claim 9, wherein X is hydrogen carboxy, $C_{1-4}$ alkoxycarbonyl, hydroxymethyl or $C_{1-5}$ alkanoyloxymethyl.

12. A compound according to claim 9, wherein X is $C_{1-4}$ alkoxycarbonyl.

13. A compound according to claim 9, wherein Y is C=0 or CH—$OR_5$ in which $R_5$ is (i) hydrogen, (ii) $C_{1-6}$ alkanoyl or (iii) carbamoyl unsubstituted or substituted by (1) $C_{1-4}$ alkyl, (2) phenyl unsubstituted or substituted by 1 to 3 members of halogen, $C_{1-4}$ alkyl, $C_{1-4}$ alkoxy, methylenedioxy, amino, nitro or hydroxy or (3) phenyl-$C_{1-4}$ alkyl unsubstituted or substituted by 1 to 3 members of halogen, $C_{1-4}$ alkyl, $C_{1-4}$ alkoxy, methylenedioxy, amino nitro or hydroxy.

14. A compound according to claim 9, wherein Y is hydroxymethylene.

15. A compound according to claim 9, wherein m is 0.

16. A compound according to claim 9, wherein n is an integer of 2 to 6.

17. A compound according to claim 9, wherein n is 3.

18. A compound according to claim 9, wherein $R_1$ is hydrogen and $R_2$ is $C_{1-4}$ alkoxy.

19. A compound according to claim 9, wherein $R_1$ is hydrogen, $R_2$ is $C_{1-4}$ alkoxy which is attached at the 7th position of the benzoxathiepin moiety, X is $C_{1-4}$ alkoxycarbonyl, Y is hydroxymethylene, m is 0, n is 3 and W' is halogen.

20. A compound according to claim 9, which is methyl cis-4-(3-chloropropyl)-3-hydroxy-7-methyoxy-3,4-dihydro-2H-1,5-benzoxathiepin-4-carboxylate.

* * * * *